US012630545B2

(12) United States Patent
Wang

(10) Patent No.: US 12,630,545 B2
(45) Date of Patent: May 19, 2026

(54) CRYSTAL OF COMPOUND X7 HYDROCHLORIDE AND ITS PREPARATION METHOD AND APPLICATION

(71) Applicants: ORxes Therapeutics Co., Ltd., Beijing (CN); Peng Wang, Shenyang (CN)

(72) Inventor: Peng Wang, Shenyang (CN)

(73) Assignees: Peng Wang, Shenyang (CN); ORxes Therapeutics Co., Ltd., Beijing (CN)

( * ) Notice: Subject to any disclaimer, the term of this patent is extended or adjusted under 35 U.S.C. 154(b) by 431 days.

(21) Appl. No.: 18/042,108

(22) PCT Filed: Aug. 17, 2021

(86) PCT No.: PCT/CN2021/113018

§ 371 (c)(1),
(2) Date: Feb. 17, 2023

(87) PCT Pub. No.: WO2022/037580

PCT Pub. Date: Feb. 24, 2022

(65) Prior Publication Data

US 2023/0322755 A1 Oct. 12, 2023

(30) Foreign Application Priority Data

Aug. 18, 2020 (CN) ......................... 202010831132.4

(51) Int. Cl.
*C07D 417/12* (2006.01)
*A61P 9/12* (2006.01)

(52) U.S. Cl.
CPC .............. *C07D 417/12* (2013.01); *A61P 9/12* (2018.01); *C07B 2200/13* (2013.01)

(58) Field of Classification Search
CPC ................................ A61P 9/12; C07D 417/12
See application file for complete search history.

(56) References Cited

U.S. PATENT DOCUMENTS

2015/0297586 A1 10/2015 Zhou et al.

FOREIGN PATENT DOCUMENTS

| | | | |
|---|---|---|---|
| CN | 103833642 | A | 6/2014 |
| CN | 103833658 | A | 6/2014 |
| CN | 110478351 | A | 11/2019 |
| EP | 2924032 | A1 | 9/2015 |
| EP | 2924033 | A1 | 9/2015 |
| WO | WO-2014079155 | A1 | 5/2014 |
| WO | WO-2022037580 | A1 | 2/2022 |

OTHER PUBLICATIONS

"Japanese Application Serial No. 2023512347 Office Action Mailed on Mar. 10, 2025", w English Translation, 6 pgs.
Hirayama, Noriaki, "Pharmaceutical Crystallization Methods", Chapter 4 from Handbook for Producing Crystals of Organic Compounds—principles and Kow-how, (2008), 16 pgs.
"International Application No. PCT/CN2021/113018, International Search Report and Written Opinion mailed Oct. 8, 2021", (Oct. 8, 2021), 9 pgs.
"European Application No. 21857672.6, European Search Report dated Aug. 21, 2024", (Aug. 21, 2024), 9 pgs.
Fujiwara, Mitsuko, et al., "First-Principles and Direct Design Approaches for the Control of Pharmaceutical Crystallization", Journal of Process Control 15 (2005) 493-504, (2005), 493-504.
Morissette, Sherry L., et al., "High-throughput crystallization: polymorphs, salts, co-crystals and solvates of pharmaceutical solids", Advanced Drug Delivery Reviews 56 (2004) 275-300, (2004), 275-300.
Variankaval, Narayan, et al., "From Form to Function: Crystallization of Active Pharmaceutical Ingredients", AIChE Journal, vol. 54, No. 7, (Jun. 3, 2008), 1682-1688.
"Chinese Application No. 202010831132.4, First Office Action dated Jan. 4, 2024", (Jan. 4, 2024), 4 pgs.

*Primary Examiner* — Jared Barsky
(74) *Attorney, Agent, or Firm* — Schwegman Lundberg & Woessner, P.A.

(57) ABSTRACT

1. The present invention relates to the crystal of compound X7 hydrochloride and its preparation method and application. The 2θ diffraction angle of the X-ray powder diffraction diagram of the crystal of compound X7 hydrochloride exhibits characteristic diffraction peaks in the range of 5°~35°. The crystal of the compound X7 hydrochloride has better physical and chemical properties.

Formula (I)

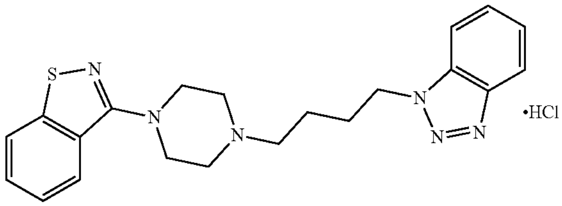

•HCl

6 Claims, 7 Drawing Sheets

CRYSTAL OF COMPOUND X7 HYDROCHLORIDE AND ITS PREPARATION METHOD AND APPLICATION

PRIORITY CLAIM TO RELATED APPLICATIONS

This application is a U.S. national stage filing under 35 U.S.C. § 371 from International Application No. PCT/CN2021/113018, filed on 17 Aug. 2021, and published as WO2022/037580 on 24 Feb. 2022, which claims the benefit under 35 U.S.C. 119 to Chinese Application No. 202010831132.4, filed on 18 Aug. 2020, the benefit of priority of each of which is claimed herein, and which applications and publication are hereby incorporated herein by reference in their entirety.

TECHNICAL FIELD OF THE INVENTION

The present invention relates to the technical field of pharmaceutical chemistry, in particular, to the crystal of compound X7 hydrochloride and its preparation method and application.

BACKGROUND OF THE INVENTION

The compound X7 hydrochloride has a strong vasodilator effect, a definite hypotensive effect with a quick onset, accompanied by a mild heart rate slowing effect, which does not affect the cardiac conduction system, and it produces a beneficial effect on hemodynamics. Its long-term administration has a protective effect on organ damage caused by hypertension. As a pharmaceutical active ingredient, the crystal structure often affects the chemical and physical stability of the drug. Different crystallization and storage conditions may lead to changes in the crystal structure of the compound, sometimes accompanied by other crystal forms. Therefore, further investigation is necessary to find crystals with better physical and chemical properties.

SUMMARY OF THE INVENTION

The present invention proposes a crystal of compound X7 hydrochloride and its preparation method and application. This crystal of compound X7 hydrochloride has better physical and chemical properties.

Based on the above purpose, one aspect of the invention provides a crystal of compound X7 hydrochloride, and the 2θ diffraction angle of the X-ray powder diffraction diagram of the crystal has characteristic diffraction peaks in the range of 5°~35°.

Wherein the structural formula of the compound X7 hydrochloride is shown in formula (I):

Formula (I)

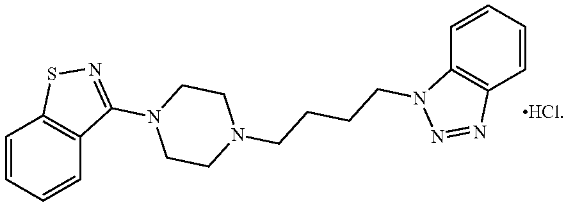

In the preferred embodiment of the invention, the crystal of compound X7 hydrochloride comprises crystal form A, and the 2θ diffraction angle of the X-ray powder diffraction diagram of crystal form A exhibits characteristic diffraction peaks at 15.12±0.2°, 11.57±0.2°, and 21.03±0.2°.

Preferably, the 2θ diffraction angle of the X-ray powder diffraction diagram of crystal form A exhibits characteristic diffraction peaks at 26.01±0.2°, 17.92±0.2°, and 27.89±0.2°.

More preferably, the 2θ diffraction angle of the X-ray powder diffraction diagram of crystal form A exhibits characteristic diffraction peaks at 25.34±0.2°, 19.96±0.2°, 12.49±0.2°, 30.64±0.2°, 7.57±0.2°, 31.11±0.2°, and 9.99±0.2°.

In the preferred embodiment of the invention, the thermogravimetric analysis diagram of crystal form A exhibits a weight: loss of 0.8±0.5% in the range of 30.0~155.0° C.

And/or, the differential scanning calorimetry of crystal form A exhibits endothermic peaks in the range of 210.0~220.0° C.

And/or, crystal form A is crystal free.

In the preferred embodiment of the invention, the crystal of compound X7 hydrochloride comprises crystal form B, and the 2θ diffraction angle of the X-ray powder diffraction diagram of crystal form B exhibits characteristic diffraction peaks at 7.38±0.2°, 13.19±0.2°, and 16.99±0.2°.

Preferably, the 2θ diffraction angle of the X-ray powder diffraction diagram of crystal form B exhibits characteristic diffraction peaks at 25.57±0.2°, 14.48±0.2°, and 25.05±0.2°.

More preferably, the 2θ diffraction angle of the X-ray powder diffraction diagram of crystal form B exhibits characteristic diffraction peaks at 19.86±0.2°, 23.08±0.2°, and 21.38±0.2°.

2. In the preferred embodiment of the invention, the thermogravimetric analysis diagram of crystal form B exhibits a weight loss of 8.0~12.0% in the range of 29.0~72.0° C.

And/or, the differential scanning calorimetry of crystal form B exhibits endothermic peaks in the ranges of 60.0~80.0° C. and 195.0~215.0° C. and exothermic peaks in the range of 125.0~145.0° C.

And/or, the crystal form B is hydrate.

In the preferred embodiment of the invention, the crystal of compound X7 hydrochloride comprises crystal form C, and the 2θ diffraction angle of the X-ray powder diffraction diagram of crystal form C exhibits characteristic diffraction peaks at 8.26±0.2°, 15.68±0.2°, and 14.03±0.2°.

Preferably, the 2θ diffraction angle of the X-ray powder diffraction diagram of crystal form C exhibits characteristic diffraction peaks at 21.25 10±0.2°, 25.30±0.2°, and 13.43±0.2°.

More preferably, the 2θ diffraction angle of the X-ray powder diffraction diagram of crystal form C exhibits characteristic diffraction peaks at 15.91±0.2°, 207.59±0.2°, 23.64±0.2°, 28.70±0.2°, 16.59±0.2°, 21.73±0.2°, 19.28±0.2°, 2.13±0.2°, 38.46±0.2°, 33.57±0.2°, 25.78±0.2°, 30.31±0.2°, and 34.30±0.2°.

In the preferred embodiment of the invention, the thermogravimetric analysis diagram of crystal form C exhibits a weight loss of 1.5~2.5% in the range of 27.0~190.0° C.

And/or, the differential scanning calorimetry of crystal form C exhibits endothermic peaks in the range of 128.0~460.0° C. and exothermic peaks in the range of 201.0~210.0° C.

And/or, the crystal form C is crystal free.

In the preferred embodiment of the invention, the crystal of compound X7 hydrochloride comprises crystal form D, and the 2θ diffraction angle of the X-ray powder diffraction diagram of crystal form D exhibits characteristic diffraction peaks at 15.69±0.2°, 24.98±0.2°, and 8.69±0.2°.

Preferably, the 2θ diffraction angle of the X-ray powder diffraction diagram of crystal form D exhibits characteristic diffraction peaks at 15.12±0.2°, 12.67±0.2°, and 22.11±0.2°.

More preferably, the 2θ diffraction angle of the X-ray powder diffraction diagram of crystal form D exhibits characteristic diffraction peaks at 21.40±0.2°, 25.62±0.2°, 27.89±0.2°, 19.39±0.2°, 18.38±0.2°, 6.28±0.2°, 13.85±0.2°, 27.39±0.2°, 28.94±0.2°, 18.88±0.2°, 35.84±0.2°, 33.36±0.2°, 31.68±0.2°, and 30.65±0.2°.

In the preferred embodiment of the invention, the thermogravimetric analysis diagram of crystal form D exhibits a weight loss of 2.0~2.5% in the range of 30.0~190.0° C.

And/or, the differential scanning calorimetry of crystal form D exhibits endothermic peaks in the range of 200.0~210.0° C.

And/or, the crystal form D is crystal free.

In the preferred embodiment of the invention, the crystal of the compound X7 hydrochloride comprises crystal form E, and the 2θ diffraction angle of the X-ray powder diffraction diagram of crystal form E exhibits characteristic diffraction peaks at 23.08±002©, 19.05±0.2°, and 13.01±0.2°.

Preferably, the 2θ diffraction angle of the X-ray powder diffraction diagram of crystal form E exhibits characteristic diffraction peaks at 26.12±0.2°, 21.56±0.2°, and 11.81±0.2°.

More preferably, the 2θ diffraction angle of the X-ray powder diffraction diagram of crystal form E exhibits characteristic diffraction peaks at 15.36±0.2°, 23.83±0.2°, and 24.75±0.2°.

Further preferably, the 2θ diffraction angle of the X-ray powder diffraction diagram of crystal form E exhibits characteristic diffraction peaks at 18.75±0.2°, 9.57±0.2°, 9.81±0.2°, 22.71±0.2°, 24.28±0.2°, 16.76±0.2°, 28.19±0.2°, 19.72±0.2°, 20.77±0.2°, and 16.40±0.2°.

In the preferred embodiment of the invention, the crystal of compound X7 hydrochloride comprises crystal form F, and the 2θ diffraction angle of the X-ray powder diffraction diagram of crystal form F exhibits characteristic diffraction peaks at 11.74±0.2°, 5.77±0.2°, and 15.66±0.2°.

Preferably, the 2θ diffraction angle of the X-ray powder diffraction diagram of crystal form F exhibits characteristic diffraction peaks at 23.79±0.2°, 26.51±0.2°, 13.81±0.2°, 28.49±0.2°, 30.11±0.2°, 20.25±0.2°, 17.74±0.2°, 8.82±0.2°, 18.79±°, and 33.04±°.

In the preferred embodiment of the invention, the thermogravimetric analysis diagram of crystal form F exhibits a weight loss of 8.0~8.5% in the range of 25.0~90.0° C.

And/or, the differential scanning calorimetry of crystal form F exhibits endothermic peaks in the ranges of 50.0~80.0° C., 190.0~205.0° C., and 206.0~215.0° C.

And/or, the crystal form F is hydrate.

Based on the same inventive concept, another aspect of the invention provides a method for preparing the crystal of compound X7 hydrochloride, (a) the preparation method of crystal form A comprises:

Dissolving the compound X7 hydrochloride in the first good solvent, then adding the first anti-solvent drop-wise, and collecting the precipitated solid to obtain crystal form A.

Preferably, the first good solvent is selected from at least one of methanol, trichloromethane, dimethyl sulfoxide, or N-methylpyrrolidone.

And/or, preferably, the first anti-solvent is selected from at least one of acetone, isopropyl acetate, 2-methyltetrahydrofuran, methyl isobutyl ketone, toluene, isopropanol, methyl tert-butyl ether, acetonitrile, or ethyl acetate.

Or, (b) the preparing method of crystal form A comprises:

Placing the open container containing compound X7 hydrochloride in the sealed container containing the first solvent, letting it stand still, and collecting the solid to obtain crystal form A.

Preferably, the first: solvent is selected from at: least one of water, dichloromethane, ethanol, methanol, acetonitrile, tetrahydrofuran, trichloromethane, acetone, dimethyl sulfoxide, ethyl acetate, 1,4-dioxane, or isopropanol.

Preferably, the "letting it stand still" means 6 to 10 days at room temperature.

Or, (c) the preparing method of crystal form A comprises:

Placing compound X7 hydrochloride in a container, adding a second solvent to dissolve compound X7 hydrochloride in the second solvent, preparing a clear solution, then slowly volatilizing, and collecting the solid to obtain crystal form A.

Preferably, the second solvent is selected from at least one of methanol, ethanol, dichloromethane, trichloromethane, the mixed solvent of methanol and acetone (v/v, 0.5~1.5:4 the mixed solvent of ethanol and acetonitrile (v/v, 3.5~4.5: 1), or the mixed solvent of dichloromethane and tetrahydrofuran (v/v, 3.5~4.5:1).

Or, (d) the preparing method of crystal form A comprises:

Dissolving the compound X7 hydrochloride in the third solvent, then heating to make the solution clear and then filtering, gradually cooling the filtrate, and collecting the precipitated solid to obtain crystal form A.

Preferably, the third solvent is selected from at least one of methanol, chloroform, acetonitrile, the mixed solvent of methanol and isopropyl acetate (v/v, 0.5~1.5:1), the mixed solvent of ethanol and methyl tert-butyl ether (NA, 3.5~4.5: 1), or the mixed solvent of trichloromethane and acetonitrile (v/v, 0.5~1.5:1).

And/or, preferably, the heating is 40~60° C. for 1.5~2.5 h.

And/or, preferably, the gradual cooling is to cool the filtrate from 40~60° C. to 3~8° C. at a cooling rate of 0.05~0.1 r/min.

Or, (e) the preparing method of crystal form A comprises:

Adding a fourth solvent to compound X7 hydrochloride to obtain a turbid solution, stirring the turbid solution, and collecting the solid by centrifugation to obtain crystal form A.

Preferably, the fourth solvent is selected from at least one of ethanol, methyl isobutyl ketone, ethyl acetate, methyl tert-butyl ether, acetonitrile, toluene, the mixed solvent of ethanol and 1,4-dioxane (v/v, 0.5~1.5:1), the mixed solvent of methyl isobutyl ketone and n-heptane (v/v, 0.5~1.5:1), the mixed solvent of isopropyl acetate and dichloromethane (v/v, 3.5~4.5:1), the mixed solvent of tetrahydrofuran and acetonitrile 0.5~1.5:1), the mixed solvent of acetone and N-methylpyrrolidone (v/v, 3.5~4.5:1), the mixed solvent of isopropanol and ethyl acetate (v/v, 0.5~1.5:1), the mixed solvent of methanol and methyl tert-butyl ether (v/v, 0.5~1.5:4 the mixed solvent of 2-methyltetrahydrofuran and trichloromethane (v/v, 3.5~4.5:1), the mixed solvent of methyl isobutyl ketone and dimethyl sulfoxide (v/v, 3.5~4.5: 1), or the mixed solvent of ethanol and water (v/v, 770~97: 3~30).

And/or, preferably, stirring the turbid solution at room temperature for 3~5 days.

Or, (f) the preparing method of crystal form A comprises:

Adding a fifth solvent to compound X7 hydrochloride to obtain a turbid solution, stirring the turbid solution at 45~55° C., and collecting the solid by centrifugation to obtain crystal form A.

Preferably, the fifth solvent is selected from at least one of ethanol, isopropanol, acetone, isopropyl acetate, 1,4-dioxane, acetonitrile, n-heptane, the mixed solvent of isopropanol and 2-methyltetrahydrofuran (v/v, 0.5~1.5:1), the mixed solvent of methyl isobutyl ketone and ethyl acetate (v/v, 0.5~1.5:1), the mixed solvent of trichloromethane and n-heptane (v/v, 3.5~4.5:1), the mixed solvent of ethanol and acetone (v/v, 0.5~1.5:1), the mixed solvent of acetonitrile and water (v/v, 0.5~1.5:1), the mixed solvent of isopropyl acetate and N, N-dimethylacetamide (v/v, 8.5~9.5:1), the mixed solvent of methyl left-butyl ether and N-methylpyrrolidone (v/v, 8.5~9.5:1), the mixed solvent of acetone and acetonitrile (v/v, 0.5~1.5:1), or the mixed solvent of 2-methyltetrahydrofuran and toluene (v/v, 0.5~1.5:1).

And/or, preferably, stirring the turbid solution at 45~55° C. for 3~5 days.

Or, (g) the preparing method of crystal form A comprises:

Dissolving compound X7 hydrochloride in a second good solvent to prepare a clear solution, and placing the container containing the clear solution open in a sealed container containing the second anti-solvent, letting it stand still, and collecting the precipitated solid to obtain the crystal form A.

Preferably, the second good solvent is selected from at least one of methanol, dichloromethane or trichloromethane.

And/or, preferably, the second anti-solvent is selected from at least one of ethyl acetate, 1,4-dioxane, isopropyl acetate, toluene, methyl isobutyl ketone, acetonitrile, 2-methyltetrahydrofuran, n-heptane, isopropanol, ethyl acetate, or methyl tert-butyl ether.

Or, (h) the preparing method of crystal form A comprises:

Dissolving compound X7 hydrochloride in the sixth solvent, adding the polymer, volatilizing slowly, and collecting the solid to obtain crystal form A.

Preferably, the sixth solvent is selected from at least one of methanol, dichloromethane, trichloromethane, the mixed solvent of acetonitrile and trichloromethane (v/v, 0.5~1.5:1), the mixed solvent of chloroform, acetone, and dichloromethane (v/v, 1:1~3), or the mixed solvent of ethanol and water (v/v, 0.5~1.5:1).

And/or, preferably, the high polymer includes the mixed high polymer A and mixed high polymer B. The mixed high polymer A includes polyvinylpyrrolidone, polyvinyl alcohol, polyvinyl chloride, polyvinyl acetate, hydroxypropyl methyl cellulose, and methyl cellulose Inked in equal mass; the mixed polymer B includes polycaprolactone, polyethylene glycol, polymethyl methacrylate, sodium alginate, or hydroxyethyl cellulose mixed in equal mass.

Based on the same inventive concept, another aspect of the invention provides a method for preparing the crystal of compound X7 hydrochloride; (1) the preparation method of crystal form B comprises:

Placing compound X7 hydrochloride in a container, adding the mixed solvent of acetonitrile and water (v/v, 0.5~1.5:1) to dissolve compound X7 hydrochloride in the mixed solvent, preparing a clear solution, then slowly volatilizing, and collecting the solid to obtain crystal form B.

Or, (2) the preparing method of crystal form B comprises:

Dissolving; compound X7 hydrochloride in water or ethanol, stirring and filtering, then gradually cooling the filtrate, collecting the precipitated solid, and drying at room temperature and humidity to obtain crystal form B.

Preferably, stirring for 0.5~1.5 days at 40~60° C.

And/or, preferably, the gradual cooling is to cool the filtrate from 40~60° C. to 3~8° C. at a cooling rate of 0.05~0.1 BC/min.

Or, (3) the preparing method of crystal form B comprises: Adding water to compound X7 hydrochloride to obtain a turbid solution, stirring the turbid solution, and collecting the solid by centrifugation to obtain crystal form B.

Preferably, stirring the turbid solution at room temperature for 3~5 days.

Based on the same inventive concept, another aspect of the invention provides a method for preparing the crystal of compound X7 hydrochloride; the preparation method of crystal form C comprises:

Dissolving compound X7 hydrochloride in water, stirring and filtering, then gradually cooling the filtrate, collecting the precipitated solid, and drying under vacuum at room temperature to obtain crystal form C.

Preferably, stirring for 2~4 h at 40~60° C.

And/or, preferably, the gradual cooling is to cool the filtrate from 40~60° C. to 3~8° C. at a cooling rate of 0.05~0.1 r/min.

And/or, preferably, the drying time under vacuum is 0.5~1.5 days. Based on the same inventive concept, another aspect of the invention provides a method for preparing the crystal of compound X7 hydrochloride; (1) the preparation method of crystal form D comprises:

Placing compound X7 hydrochloride in a container, adding the mixed solvent of trichloromethane and n-heptane (v/v, 0.5~1.5:1) to dissolve compound X7 hydrochloride in the mixed solvent, preparing a clear solution, then slowly volatilizing, and collecting the solid to obtain crystal form D.

Or, (2) the preparing method of crystal form D comprises:

Dissolving compound X7 hydrochloride in water to prepare a clear solution, and placing the container containing the clear solution open in a sealed container containing acetone, letting it stand still, and collecting the precipitated solid to obtain crystal form D.

Based on the same inventive concept, another aspect of the invention provides a method for preparing the crystal of compound X7 hydrochloride; the preparation method of crystal form E comprises:

Dissolving the compound X7 hydrochloride in water, then heating to make the solution clear and then filtering, gradually cooling the filtrate, and collecting the precipitated solid to obtain crystal form E.

Preferably, heating for 40~60 for 1.5~2.5 h.

And/or, preferably, the gradual cooling is to cool the filtrate from 40~60° C. to 3~8 at a cooling rate of 0.05~0.1 r/min.

Based on the same inventive concept, another aspect of the invention provides a method for preparing the crystal of compound X7 hydrochloride; the preparation method of crystal form F comprises:

Dissolving compound X7 hydrochloride in a mixed solvent of ethanol and water of (v/v, 4~6:2), filtering after sonification, and volatilizing the filtrate at room temperature to obtain crystal form E.

Preferably, the sonification time is 20~40 s.

In the preferred embodiment of the invention, the crystal form F is dissolved in water and stirred at room temperature to transform into crystal form B.

Or, heating the crystal form C to 155~165° C. and cooling down to room temperature to transform into crystal form D.

Or, stirring the crystal form D or C in at least one solvent selected from ethanol or trichloromethane for 2~4 days to transform into crystal form A. Preferably, the stirring temperature is the room temperature or 45~55° C.

Or, stirring the crystal form B or F in acetone or the mixed solvent of acetone and water to transform into the crystal form A, preferably, in the mixed solvent of acetone and water, the water activity ($a_w$) is ≤0.8.

Based on the same inventive concept, another aspect of the invention provides a pharmaceutical composition that comprises a crystal of compound X7 hydrochloride and a pharmaceutically acceptable carrier or excipient.

Based on the same inventive concept, another aspect of the invention provides the application of the crystal of compound X7 hydrochloride or the pharmaceutical composition in the preparation of drugs for prevention, treatment, and delay of hypertension, target organ damage caused by hypertension, and hypertension related diseases.

DETAILED DESCRIPTION OF THE INVENTION

Figure 1:
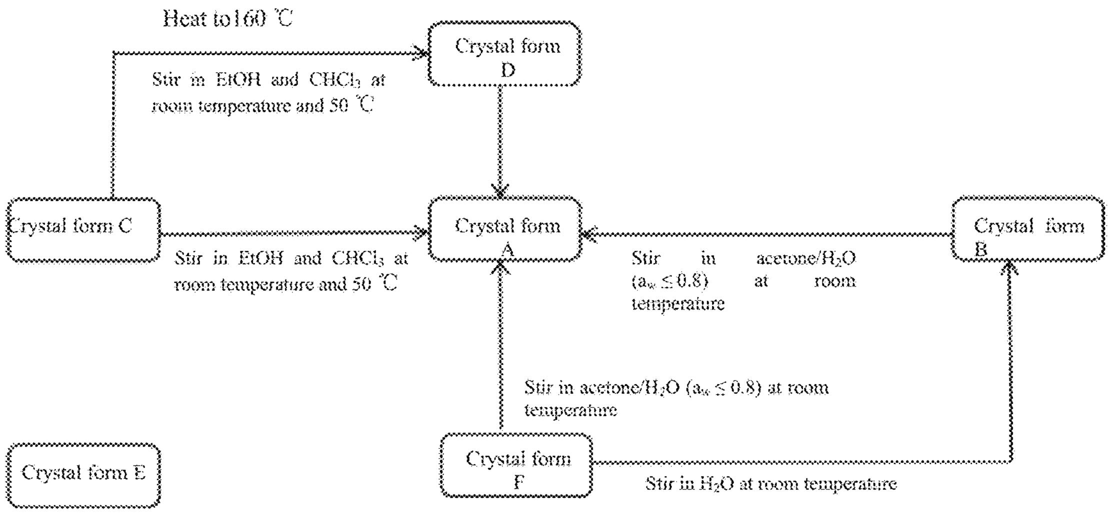
FIG. 1 is the transformation diagram of polymorphs of compound X7 hydrochloride.

It should be noted that, unless otherwise defined, the technical or scientific terms used in one or more examples of the present invention should have the general meanings understood by person having ordinary skill in the art, in the field of this disclosure.

In the present invention, unless otherwise stated, all operations are carried out at: room temperature and atmospheric pressure.

In the present invention, "room temperature" refers to (25±2)° C., and "humidity" refers to 30-80% relative air humidity.

In the present invention, relative humidity is expressed as RH, which is the percentage of water vapor content (vapor pressure) of gas (usually air) in saturated water vapor volume (saturated vapor pressure) under the same air conditions.

In the present invention, water activity is expressed as $a_w$, which is defined as the volume of free water currently available in the sample, falling in the range of 0 (absolute dry) to 1 (relative humidity 100%).

The abbreviations of solvents involved in the following examples and corresponding Chinese names are provided in Table 1.

TABLE 1

Corresponding table of solvent names

| English | Chinese | English | Chinese |
| --- | --- | --- | --- |
| MeOH | 乙醇 | 1,4-dioxane | 1,4-二氧六环 |
| EtOH Popex | 乙醇 | ACN | 乙腈 |
| IPA | 异丙醇 | DCM | 二氯甲烷 |
| acetone | 丙酮 | $CHCl_3$ | 三氯甲烷/氯仿 |
| MIBK | 甲基异丁基酮 | n-heptane | 正庚烷 |
| EtOAc | 乙酸乙酯 | toluene | 甲苯 |
| IPAc | 乙酸异丙酯 | DMSO | 二甲基亚砜 |
| MTBE | 甲基叔丁基醚 | DMAc | N,N-二甲基乙酰胺 |
| THF | 四氢呋喃 | NMP | N-甲基吡咯烷酮 |
| 2-MeTHF | 2-甲基四氢呋喃 | $H_2O$ | 水 |

The reagents in Table 1 can be purchased from Sinopharm Chemical Reagents Co., Ltd.

As described in the Background of the invention, as a pharmaceutical active ingredient, the crystal structure often affects the chemical and physical stability of the drug. Different crystallization and storage conditions may lead to changes in the crystal structure of the compound, and sometimes be accompanied by other crystal forms. Therefore, further investigation is necessary to find crystals with better physical and chemical properties. The present invention aims to screen the polymorphs of compound X7 hydrochloride and recommend the crystal form with better physical and chemical properties for subsequent investigation and development by identifying and evaluating the discovered polymorphs.

A polymorph screening test was conducted for the invention. In the polymorph screening test, the starting sample of compound X7 hydrochloride was taken as the raw material, and the methods of anti-solvent addition, gas-solid permeation, gas-liquid permeation, suspension stirring at room temperature/50° C., slow volatilization, slow cooling, and polymer induction were used to set up more than 100 crystal form screening tests. A total of 6 new crystal forms of hydrochloride were found, and are named crystal form A, B, C, D, E, and F respectively. Specific test methods and results are summarized in Table 2.

TABLE 2

Summary of polymorph screening test

| Methods | Number of tests | Solid crystal form |
| --- | --- | --- |
| Anti-solvent addition | 16 | Crystal form A, E, gelatin |
| Gas-solid permeation | 12 | Crystal form A |
| Slow volatilization | 9 | Crystal form A, B, D |
| Slow cooling | 9 | Crystal form A, B, E, gelatin |

TABLE 2-continued

Summary of polymorph screening test

| Methods | Number of tests | Solid crystal form |
|---|---|---|
| Suspension stirring at room temperature | 20 | Crystal form A, B |
| Suspension stirring at 50° C. | 16 | Crystal form A |
| Gas-liquid permeation | 12 | Crystal form A, D |
| Polymer induction | 6 | Crystal form A |
| Total | 100 | Crystal form A, B, D, E, F, gelatin |

Then, the representative samples of the new crystal forms were characterized by X-ray powder diffraction (XRPD), thermogravimetric analysis (TGA), differential scanning calorimetry (DSC) and high-performance liquid chromatography/ion chromatography (HPLC/IC). The specific characterization results are summarized in Table 3.

TABLE 3

Summary of characterization results of compound X7

| Crystal form | TGA weight loss (wt %) | DSC endothermic peak (° C., starting temperature) | Mole ratio (acid/base) | Crystal form identification |
|---|---|---|---|---|
| Crystal form A | 0.8 (150° C.) | 211.7 | 1.0:1 | Anhydrous crystal form |
| Crystal form B | 8.3 (70° C.) | 68.3#, 126.9*, 201.3 | 1.0:1 | Hydrate |
| Crystal form C | 1.8 (180° C.) | 134.8*, 204.6 | 1.0:1 | Anhydrous crystal form |
| Crystal form D | 2.4 (180° C.) | 204.5 | 1.0:1 | Anhydrous crystal form |
| Crystal form E | N/A | N/A | N/A | N/A |
| Crystal form F | 8.3 (80° C.) | 71.2#, 199.0, 208.9# | 1.0:1 | Hydrate |

#peak temperature.
*exothermic peak.
N/A: no characterization or identification was carried out because of the few samples obtained and the difficulty in repeating preparation.

In the present invention, the structural formula of the compound X7 hydrochloride is shown in formula (I):

Formula (I)

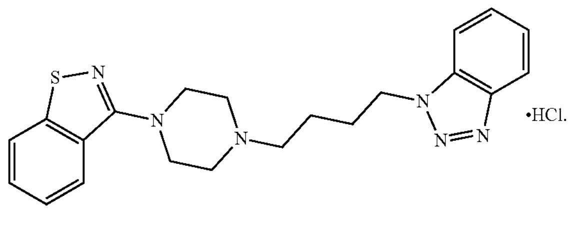

Chemical name of compound X7 hydrochloride: 3-(4-(4-(1H-benzotriazol-1-yl) butyl) piperazin-1-yl) benzoisothiazole hydrochloride, molecular formula: $C_{21}H_{24}SN_6 \cdot HCl$, molecular weight: 428.98, white powder.

In the present invention, the mutual transformation relationship between different crystal forms obtained in the screening test was studied, and the results are summarized in FIG. 1. To determine the stability relationship between the anhydrous crystal form and the hydrate, the suspension competition test was carried out for the relevant crystal forms. The results show that: 1) At room temperature (25±2° C.) and 50° C., all the physical mixtures of anhydrous crystal form A, C, and D suspended and stirred in EtOH and $CHCl_3$ for 3 days were transformed into crystal form A. 2) At room temperature, all the physical mixtures of anhydrous crystal form A and hydrate crystal forms B and F suspended and stirred in acetone/$H_2O$ ($a_w$≤0.8) were transformed into crystal form A, and after suspension and stirring in $H_2O$ ($a_w$=1), the mixtures were transformed into crystal form B. In summary, when the water activity $a_w$ is ≤0.8 at room temperature to 50° C., and at room temperature, crystal form A is a thermodynamically stable anhydrous crystal form; when water activity $a_w$=1 at room temperature, crystal form B is a more stable hydrate. Suspension competition test results are summarized in Table 4.

TABLE 4

Summary of suspension competition test results

| Starting crystal form | Solvent | Temperature | Solid crystal form |
|---|---|---|---|
| Crystal form A + C + D | EtOH | RT | Crystal form A |
| | | 50° C. | |
| | $CHCl_3$ 10004 | RT | |
| | | 50° C. | |
| Crystal form A + B + F | acetone | RT | Crystal form A |
| | acetone/$H_2O$ ($a_w$~0.2) | | |
| | acetone/$H_2O$ (aw~0.4) | | |
| | acetone/$H_2O$ (aw~0.6) | | |
| | acetone/$H_2O$ (aw~0.8) | | |
| | $H_2O$ | | Crystal form B |

According to the above characterization results, anhydrous crystal form A and hydrate crystal form B were selected to test and evaluate the hygroscopicity, solid state stability, equilibrium solubility in $H_2O$ and crystal morphology. 1) Dynamic vapor sorption (DVS) test shows that at 25° C./80% RH (relative humidity), crystal form A absorbs 0.08% of water, suggesting that it has no hygroscopicity (refer to the China Pharmacopoeia 2015 (guide for drug hygroscopicity test)); crystal form B quickly changes its water absorption at 80-95% RH during adsorption and 50-30% RH during desorption, suggesting the transition between anhydrous crystal form and hydrate. 2) After crystal form A and B were stored in the sealed container at 80° C. for 1 day, and in the open container at 25° C./60% RH and 40° C./75% RH for 1 week, the physical and chemical stability was determined. The test results show that crystal form A does not undergo crystal form transformation and chemical purity reduction under these 3 conditions; the chemical purity of crystal form B does not decrease under these 3 conditions, and the crystal form remains unchanged after storing at 25° C./60% RH for 1 week. 3) The equilibrium solubility of crystal form A and B stored in $H_2O$ for 24 hours is 3.8 and 3.4 mg/mL, respectively, and the crystal form remains unchanged after the solubility test. 4) PLM results show that crystal form A is an acicular crystal, and crystal form B is a granular crystal with particle size <20 μm. The stability study shows that crystal form A has good physical and chemical stability.

Comprehensively considering the stability relationship between crystal forms and the evaluation results of solid-state properties, anhydrous crystal form A is recommended as the preferred crystal form for further development.

The molecular weight of the polymer in the present invention is calculated by using the weight average molecular weight, which is determined by using the gel permeation chromatography (GPC) according to the National Standard of the People's Republic of China (GB/T 21863-2008) (equivalent to the German Standard DIN55672-1:2007 Gel permeation chromatography (GPC)—Part 1: Tetrahydrofuran (THF) as eluent). Specifically, the weight average molecular weight is 8,000~700,000 for polyvinylpyrrolidone, 16,000~20,000 for polyvinyl alcohol, 50,000~110,000 for polyvinyl chloride, 20,000~30,000 for polyvinyl acetate, 400,000~675,000 for hydroxypropyl methylcellulose, 18,000~200,000 for methyl cellulose, 50,000~70,000 for polycaprolactone, 200~600 for polyethylene glycol, 80,000~200,000 for polymethyl methacrylate, 300,000~400,000 for alginate, and 700,000~800,000 for hydroxyethyl cellulose. All these reagents can be purchased from Ashland Chemical (Nanjing) Co., Ltd.

It should be noted that in addition to the preparation methods of crystal form C in Table 2, crystal form C can also be prepared by the following method:

Dissolving compound X7 hydrochloride in water, stirring and filtering, then gradually cooling the filtrate, collecting the precipitated solid, and drying under vacuum at room temperature to obtain crystal form C. Preferably, stir for 2~4 h at 40~60° C.

And/or, preferably, the gradual cooling is to cool the filtrate from 40~60° C. to 3~8° C. at a cooling rate of 0.05~0.1° C./min.

And/or, preferably, the drying time under vacuum is 0.5~1.5 days.

Similarly, crystal form F can also be prepared by the following method:

Dissolving compound X7 hydrochloride in a mixed solvent of ethanol and water of (v/v, 4~6:2), filtering after sonification, and volatilizing the filtrate at room temperature to obtain the crystal form F; preferably, the sonification time is 20~40 s.

In the preferred embodiment of the invention, as shown in FIG. 1, the crystal forms can be transformed mutually; specifically, crystal form F can be dissolved in water and stirred at room temperature to transform into crystal form B.

Or, heating crystal form C to 155~165° C. and cooling to room temperature to transform into crystal form D; preferably, heating crystal form C to 160° C. and cooling to room temperature to transform into crystal form 0.

Or, stirring crystal form D or C in at least one solvent selected from EtOH or $CHCl_3$ for 2~4 days to transform into crystal form A; preferably, the stirring temperature is the room temperature or 45~55° C.; preferably, the stirring temperature is the room temperature or 50° C.

Or, stirring crystal form B or F in acetone or the mixed solvent of acetone and $H_2O$ to transform into crystal form A, preferably, in the mixed solvent of acetone and $H_2O$, the water activity ($a_w$) is ≤0.8.

Based on the same inventive concept, another aspect of the invention provides a pharmaceutical composition, which comprises a crystal of compound X7 hydrochloride and a pharmaceutically acceptable carrier or excipient.

In the present invention, "pharmaceutically acceptable carrier" refers to one or more compatible solid or liquid fillers or gel substances that are suitable for human use and must have sufficient purity and low toxicity. "Compatibility" means that each component of the composition can be mixed with the active components and other components of the invention, without significant reduction in the efficacy of the active ingredients. Some examples of pharmaceutically acceptable carriers include cellulose and its derivatives (e.g., sodium carboxymethyl cellulose, sodium ethyl cellulose, cellulose acetate, etc.), gelatin, talc, solid lubricants (e.g., stearic acid, magnesium stearate), calcium sulfate, vegetable oils (e.g., soybean oil, sesame oil, peanut oil, olive oil, etc.), polyols e.g., propylene glycol, glycerin, mannitol, sorbitol, etc.), emulsifiers (e.g., Tween), wetting reagents e.g., sodium dodecyl sulfate), colorant, flavoring agent, stabilizer, antioxidant, preservatives, etc.

The dosage forms of the pharmaceutical composition of the present invention include tablets, capsules, granules, powders, pills, or films. In these solid dosage forms, the active ingredient is mixed with at least one conventional inert excipient (or carrier), such as sodium citrate or dicalcium phosphate, or with the following ingredients; (a) fillers or compatibilizers, including starch, lactose, sucrose, glucose, mannitol, and silicic acid; (b) adhesives, including hydroxymethyl cellulose, alginate, gelatin, polyvinylpyrrolidone, sucrose, and gum arabic; (c) humectants, including glycerin; (d) disintegrators, including agar, calcium carbonate, potato starch or cassava starch, and sodium carbonate; (e) lubricants, including talc, calcium stearate, magnesium stearate, or a mixtures thereof.

Based on the same inventive concept, another aspect of the invention provides the application of the crystal of compound X7 hydrochloride or the pharmaceutical composition in the preparation of drugs for prevention, treatment, and delay of hypertension, target organ damage caused by hypertension, and hypertension-related diseases.

In the preferred embodiment of the invention, the target organ damage is the damage to the heart, brain, kidney, or blood vessel caused by hypertension; hypertension-related diseases include atherosclerosis, hyperlipidemia, obesity, coronary heart disease, aortic dissection and hyperglycemia, impaired glucose tolerance, metabolic syndrome, and diabetes.

In the preferred embodiment of the invention, the target organ damage is left ventricular hypertrophy, stroke, renal cortex atrophy or aortic thickening, angina pectoris, myocardial infarction, cardiac failure, renal failure, retinal arteriosclerosis, and hypertensive fund us lesions.

All test methods of the present invention are general methods, comprising:

1. X-ray Powder Diffraction (XRPD) XRPD diagrams were created using PANalytical Empyrean and X 'Pert3 X-ray powder diffraction analyzer. The scanning parameters are provided in Table 5.

TABLE 5

XRPD test parameters

| Parameters | Empyrean (transmission mode) | X'Pert3 (reflection mode) | |
|---|---|---|---|
| X-ray | Cu, Kα, Kα1 (Å): 1.540598; Kα2 (Å): 1.544426 Kα2/Kα1 strength ratio: 0.50 | | |
| X-ray tube setting | 45 kV, 40 mA | 45 kV, 40 mA | 45 kV, 40 mA |
| Divergence slit | Automatic | 1/8° | 1/8° |
| Monochromator | None | None | None |
| Scanning mode | Continuous | Continuous | Continuous |
| scanning range (°2θ) | 3°~40° | 3°~40° | 3°-40° |
| Scanning step (°2θ) | 0.0167° | 0.0263° | 0.0263° |
| Scanning time (min) | 10 min 11 s | About 5 min | About 4 min 30 s |

2. Thermogravimetric Analysis (TGA) and Differential Scanning Calorimetry (DSC)

TGA and DSC diagrams were created using a TA Q500/5000 thermogravimetric analyzer and TA Q200/2000 differential scanning calorimeter, respectively. The test parameters are provided in Table 6.

TABLE 6

| TGA and DSC test parameters | | |
|---|---|---|
| Parameters | TGA | DSC |
| Method | Ramping | Ramping |
| Sample disc | Aluminum plate, open | Aluminum plate |
| Temperature range | Room temperature - set the end temperature | 25° C. - set the end temperature |
| Scanning rate (C/min) | 10 | 10 |
| Protective gas | Nitrogen | Nitrogen |

3. $^1$H Solution NMR $^1$H Solution NMR diagrams were created using a Bruker 400M NMR spectrometer with DMSO-$d_6$ as the solvent.

4. Dynamic Vapor Sorption (DVS)

Dynamic vapor sorption (DVS) curves were created using DVS Intrinsic of SMS (Surface Measurement Systems). The relative humidity at 25° C. was corrected by the deliquescence points of LiCl, Mg $(NO_3)_2$, and KCl. DVS test parameters are provided in Table 7.

TABLE 7

| DVS test parameters | |
|---|---|
| Parameters | Set value |
| Temperature | 25° C. |
| Sample amount | 10-20 mg |
| Protective gas and flow | $N_2$, 200 mL/min |
| dm/dt | 0.002%/min |
| Minimum dm/dt balance time | 10 min |
| Maximum balance time | 180 min |
| RH range | 0%-95% RH - 0% (anhydrous crystal form) Room humidity - 95%-0% RH - 95% RH (hydrate) |
| RH gradient | 10% (0%-90% RH, 90%-0% RH) 5% (90%-95% RH, 95%-90% RH) |

5. Polarizing Microscope (PLM)

PLM data were collected using Axio Lab. AI orthostatic microscope at room temperature.

The technical solutions provided by the present invention are further described in combination with specific examples. The following examples are only used to illustrate the present invention and do not limit the scope of protection of the present invention.

Example 1: Preparation Method of Compound 7

Step 1: Preparation of 4-chlorobutyl-substituted benzotriazole (1)

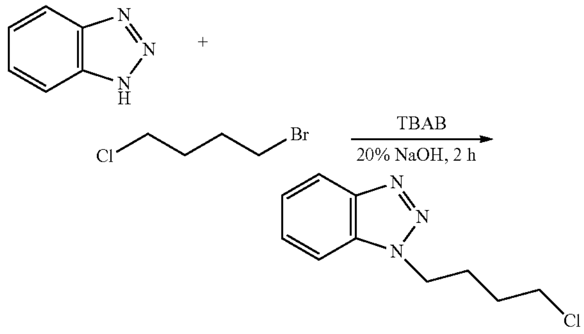

Add 24.0 g of purified water into a 100 mL reaction flask, and then add 4.8 g of sodium hydroxide for dissolution. Weigh 3.0 g of benzotriazole, 3.9 g of 1-bromo-4-chlorobutane, and 0.18 g of tetrabutylammonium bromide, mix and stir. Heat to 60° C., and stir to react for 6 h. Add 24.0 g of purified water, stir to cool to room temperature; add 31.8 g of dichloromethane, stir for 15 min and let it stand still for 15 min, separate and remove the aqueous layer to obtain the organic phase (retain); add 31.8 g of dichloromethane into water phase, stir for 15 min and let it stand still for 15 min, separate and remove the aqueous layer to obtain the organic phase (retain), mix the organic phases; treat the aqueous layer separately. Depressurize and 2θ concentrate the organic phase to obtain the oily liquid product (I).

Step 2: preparation of 3-(4-(4-(1H-benzotriazol-1-yl) butyl) piperazin-1-yl) benzoisothiazole free base (II)

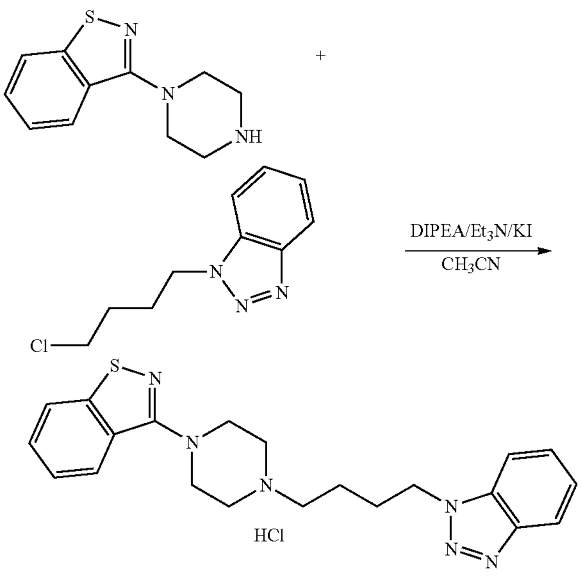

Add 15 g of acetonitrile, 1.9 g of 3-(1-piperazinyl)-1,2-benzisothiazole, 3.3 g of diisopropylethylamine, 1.4 g of potassium iodide, and 1.8 g of 1-(4-chlorobutyl)-1H-benzotriazole in a 100 mL reactor. Reflux and react for 24 h. Cool the reaction solution to room temperature, filter, concentrate the reaction solution to obtain an oily substance, add 30 mL of ethyl acetate to dissolve, extract in purified water, and depressurize and concentrate the organic phase to obtain the oily product (II).

Step 3: preparation of 3-(4-(4-(1H-benzotriazol-1-yl) butyl) piperazin-1-yl) benzoisothiazole hydrochloride (III)

Dissolve the oily product (II) obtained in Step 2 with 15 g of absolute ethanol, transfer into a 100 mL reaction bottle, drip concentrated hydrochloric acid (about 3 mL) into the reaction bottle, adjust pH=1~2, precipitate a yellow white solid, filter the solid and add 35 g of 95% ethanol, mix evenly, heat to dissolve completely, filter, and crystallize. Filter the precipitated crystal and dry to obtain 2.23 g of X7 hydrochloride. White to similar white solid, mass spectrometry test shows [M+H]+=393.2.

Example 2: Preparation of Crystal Form a and F of Compound X7 Hydrochloride by Anti-Solvent Addition Method Different solvents were used to set a total of 16 anti-solvent addition tests. Respectively weigh about 15 mg/portion of the starting sample (814802-05-A, prepared in Example 1) and add into a 20 mL vial. Add 0.8~4.0 mL of good solvent to dissolve (see Table 8), and then add the anti-solvent listed in Table 8 to the clear solution. Stir the solution while adding the anti-solvent till a solid precipitate is formed. Stop if there is no solid precipitate after adding about 10 mL of anti-solvent. Centrifuge to separate the solid and carry out XRPD test; the results are provided in Table 8. The crystal forms A, F, and gelatin were obtained in the anti-solvent addition test.

TABLE 8

Summary of anti-solvent addition test

| Test No. | Solvent | Anti-solvent | Solid crystal form |
|---|---|---|---|
| 814802-07-A1 | MeOH | acetone | Crystal form A# |
| 814802-07-A2 | | IPAc | Crystal form A |
| 814802-07-A3 | | 2-MeTHF | Crystal form A |
| 814802-07-A4 | | toluene | Crystal form A# |
| 814802-07-A5 | $CHCl_3$ | IPA | Crystal form A# |
| 814802-07-A6 | | MIBK | Crystal form A |
| 814802-07-A7 | | toluene | Crystal form A |
| 814802-07-A8 | | MTBE | Crystal form A |
| 814802-07-A9 | DMSO | IPA | Crystal form A* |
| 814802-07-A10 | | EtOAc | Crystal form A |
| 814802-07-A11 | | acetone | Crystal form A* |
| 814802-07-A12 | NMP | 1,4-dioxane | Gelatin# |
| 814802-07-A13 | | ACN | Crystal form A# |
| 814802-07-A14 | | IPAc | Crystal form A* |
| 814802-07-A15 | $H_2O$ | EtOH | Crystal form F# |
| 814802-07-A16 | | 1,4-dioxane | Gelatin# |

*If no solid precipitate is formed after adding 10 mL of anti-solvent, transfer to 5° C. and stir.
#If no solid precipitate is formed after adding 10 mL of anti-solvent, transfer to 5° C., stir and clarify, and transfer to room temperature for volatilization.

Example 3: Preparation of Crystal Form a of Compound X7 Hydrochloride by Gas-Solid Infiltration Method Different solvents were used to set a total of 12 gas-solid diffusion tests. Weigh about 10 mg of each starting sample (814802-05-A, prepared in Example 1) and add into a 3 mL vial, add about 4 mL of solvent into a 20 mL vial, place the 3 mL vial into a 20 mL open vial, and then seal the 20 mL vial. After letting it stand still at room temperature for 8 days, collect the solid and carry out XRPD test. The test results are provided in Table 9. The crystal form A was obtained in the gas-solid permeability test.

TABLE 9

Summary of gas-solid permeability test

| Test No. | Solvent | Solid crystal form |
|---|---|---|
| 814802-08-A1 | $H_2O$ | Crystal form A |
| 8-14802-08-A2 | DCM | Crystal form A |
| 814802-08-A3 | EtOH | Crystal form A |
| 814802-08-A4 | MeOH | Crystal form A |
| 814802-08-A5 | ACN | Crystal form A |
| 814802-08-A6 | THF | Crystal form A |
| 814802-08-A7 | $CHCl_3$ | Crystal form A |
| 814802-08-A8 | acetone | Crystal form A |
| 814802-08-A9 | DMSO | Crystal form A |
| 814802-08-A10 | EtOAc | Crystal form A |
| 814802-08-A11 | 1,4-dioxane | Crystal form A |
| 814802-08-A12 | IPA | Crystal form A |

Example 4: Preparation of Crystal Form a, B, and D of Compound X7 Hydrochloride by Slow Volatilization Method Different solvent systems were used to set a total of 9 slow volatilization tests. Weigh about 15 mg of the sample (814802-05-A, prepared in Example 1) and add into a 3 vial, add 1.0-3.0 mL of the solvent in Table 10, shake and filter to collect the supernatant, seal the vials containing the clear solution with a sealing film and prick several small holes on the film, and place at room temperature to slowly volatilize. After the solvent is completely volatilized, collect the obtained solid and carry out the XRPD test. The test results are provided in Table 10. The crystal form A, B, and D were obtained in the slow volatilization test.

TABLE 10

Summary of slow volatilization test

| Test No. | Solvent (v/v) | Solid crystal form |
|---|---|---|
| 814802-09-A1 | MeOH | Crystal form A |
| 814802-09-A2 | EtOH | Crystal form A |
| 814802-09-A3 | DCM | Crystal form A |
| 814802-09-A4 | $CHCl_3$ | Crystal form A |
| 814802-09-A5 | MeOH/acetone (1:1) | Crystal form A |
| 814802-09-A6 | EtOH/can (4:1) | Crystal form A |
| 814802-09-A7 | DCM/THF (4:1) | Crystal form A |
| 814802-09-A8 | $CHCl_3$/n-heptane (1:1) | Crystal form D |
| 814802-09-can | ACN/$H_2O$ (1:1) | Crystal form B |

Example 5: Preparation of Crystal Form a, B, and E of Compound X7 Hydrochloride by Slow Cooling Method Weigh about 15 mg of each sample (814802-05-A, prepared in Example 1) and add into a 5 mL vial, add 0.6~4.0 mL of the solvent in Table 11, stir at 50° C. for about 2 h, and then filter to collect the filtrate. Place the filtrate in a biochemical incubator, reduce the temperature from 50° C. to 5° C. at a cooling rate of 0.1° C./min, and collect the solid precipitate and carry out XRPD test. Test results are provided in Table 11. The crystal form A, B, E, and gelatin were obtained in the slow cooling test.

TABLE 11

Summary of slow cooling test

| Test No. | Solvent (v/v) | Solid crystal form |
|---|---|---|
| 814802-10-A1& | MeOH | Crystal form A# |
| 814802-10-A2 | EtOH | Crystal form B# |
| 814802-10-A3 | $CHCl_3$ | Crystal form A# |
| 814802-10-A4 | ACN | Crystal form A |
| 814802-10-A5 | $H_2O$ | Crystal form E# |
| 814802-10-A6 | MeOH/IPAc (1:1) | Crystal form A* |
| 814802-10-A7 | EtOH/MTBE (4:1) | Crystal form A* |
| 814802-1O-A8 | $CHCl_3$/ACN (1:1) | Crystal form A |
| 814802-10-A9 | DMAc/toluene (1:1) | Gelatin# |

*slowly cool and clarify, transfer to −20° C. to precipitate the solid.
#slowly cool and clarify, transfer to −20° C. but no solid was precipitated, then transfer to room temperature to volatilize.
&add 34.3 mg of sample (814802-05-A).

Example 6: Preparation of Crystal Form A and B of Compound X7 Hydrochloride by Suspension Stirring Method at Room Temperature Weigh about 15 mg of each starting sample (814802-05-A, prepared in Example 1) and add into an HPLC vial, add 0.3 mL of the solvent in Table 12, place the obtained turbid solution at room temperature and magnetically stir (~1000 rpm) for about 4 days, centrifuge and separate the solid and carry out XRPD test. Test results are provided in Table 12. Crystal form A and B were obtained in the suspension mixing test at: room temperature.

TABLE 12

Summary of suspension stirring test at room temperature.

| Test No. | Solvent (v/v) | Solid crystal form |
|---|---|---|
| 814802-11-A1 | EtOH | Crystal form A |
| 814802-11-A2 | MIBK | Crystal form A |
| 814802-11-A3 | EtOAc | Crystal form |
| 814802-11-A4 | MTBE | Crystal form A |
| 814802-11-A5 | ACN | Crystal form A |

TABLE 12-continued

Summary of suspension stirring test at room temperature.

| Test No. | Solvent (v/v) | Solid crystal form |
|---|---|---|
| 814802-11-A6 | toluene | Crystal form A |
| 814802-11-A7 | $H_2O$ | Crystal form B |
| 814802-11-A8 | EtOH/1,4-dioxane (1:1) | Crystal form A |
| 814802-11-A9 | MIBK/n-heptane (1:1) | Crystal form A |
| 814802-11-A10 | IPAc/DCM (4:1) | Crystal form A |
| 814802-11-A11 | THE/ACN (1:1) | Crystal form A |
| 814802-11-A12 | acetone/NMP (4:1) | Crystal form A |
| 814802-11-A13 | IPA/EtOAc (1:1) | Crystal form A |
| 814802-11-A14 | MeOH/MTBE (1:1) | Crystal form A |
| 814802-11-A15 | 2-MeTHF/$CHCl_3$ (4:1) | Crystal form A |
| 814802-11-A16 | MIBK/DMSO (4:1) | Crystal form A |
| 814802-11-A17 | EtOH/$H_2O$ (aw~0.2, 97:3) | Crystal form A |
| 814802-11-A18 | EtOH/$H_2O$ (aw~0.4, 93:7) | Crystal form A |
| 814802-11-A19 | EtOH/$H_2O$ (aw~0.6, 86:14) | Crystal form A |
| 814802-11-A20 | EtOH/$H_2O$ (aw~0.8, 70:30) | Crystal form A* |

*stir for 4 days and clarify, add 20.3 mg of sample (814802-05-A), continue to stir for 2 days and carry out XRPD test.

Example 7: Preparation of Crystal Form a of Compound X7 Hydrochloride by Suspension Stirring Method at 50

Weigh about 20 mg of each starting sample (814802-05-A, prepared in Example 1) and add into an HPLC vial, add 0.3 mL of the solvent described in Table 13, place the obtained turbid solution at 50° C. and magnetically stir (~1000 rpm) for about 4 days, centrifuge and separate the solid, and carry out XRPD test. Test results are provided in Table 13. Crystal form A was obtained in the suspension mixing test.

TABLE 13

Summary of suspension stirring test at 50° C.

| Test No. | Solvent (v/v) | Solid crystal form |
|---|---|---|
| 814802-12-A1 | EtOH | Crystal form A |
| 814802-12-A2 | IPA | Crystal form A |
| 814802-12-A3 | acetone | Crystal form A |
| 814802-12-A4 | IPAc | Crystal form A |
| 814802-12-A5 | 1,4-dioxane | Crystal form A |
| 814802-12-A6 | ACN | Crystal form A |
| 814802-12-A7 | n-heptane | Crystal form A |
| 814802-12-A8 | IPA/2-MeTHF (1:1) | Crystal form A |
| 814802-12-A9 | MIBK/EtOAc (1:1) | Crystal form A |
| 814802-12-A10 | $CHCl_3$/n-heptane (1:4) | Crystal form A |
| 814802-12-A11 | EtOH/acetone (1:1) | Crystal form A |
| 814802-12-A12 | ACN/$H_2O$ (1:1) | Crystal form A |
| 814802-12-A13 | IPAc/DMAc (9:1) | Crystal form A |
| 814802-12-A14 | MTBE/NMP (9:1) | Crystal form A |
| 814802-12-A15 | acetone/ACN (1:1) | Crystal form A |
| 814802-12-A16 | 2-MeTHE/toluene (1:1) | Crystal form A |

*stir for 4 days and clarify, add 40.3 mg of sample (814802-05-A), stir and then continue to clarify, transfer to room temperature to volatilize.

Example 8: Preparation of Crystal Form A and D of Compound X7 Hydrochloride by Gas-Liquid Permeation Method Weigh about 15 mg of each starting sample (814802-05-A, prepared in Example 1) and dissolve in 1.2~2.4 mL of good solvent, filter the filtrate and transfer into a 3 mL vial, then take another 20 mL vial and add about 4 mL of anti-solvent, place the 3 mL open vial containing the filtrate behind the 20 mL vial, seal the 20 mL vial and leave it at room temperature. When a solid precipitate is observed, separate the solid, collect the solid, and carry out XRPD test. The test results are provided in Table 14. The crystal form A and D were obtained in the gas-liquid permeability test.

TABLE 14

Summary of gas-liquid permeability test

| Test No. | Solvent | Anti-solvent | Solid crystal form |
|---|---|---|---|
| 814802-13-A1 | MeOH | EtOAc | Crystal form A |
| 814802-13-A2 | | 1,4-dioxane | Crystal form A |
| 814802-13-A3 | | IPAc | Crystal form A |
| 814802-13-A4 | | toluene | Crystal form A |
| 814802-13-A5 | DCM | MIBK | Crystal form A |
| 814802-13-A6 | | ACN | Crystal form A |
| 814802-13-A7 | | 2-MeTHF | Crystal form A |
| 814802-13-A8 | | n-heptane | Crystal form A |
| 814802-13-A9 | $CHCl_3$ | IPA | Crystal form A |
| 814802-13-A10 | | EtOAc | Crystal form A |
| 814802-13-A11 | | MTBE | Crystal form A |
| 814802-13-A12 | $H_2O$ | acetone | Crystal form D* |

*If no solid precipitates after 6 days, transfer to room temperature for volatilization.

Example 9: Preparation of Crystal Form A of Compound X7 Hydrochloride by Polymer Induction Method Weigh about 15 mg of each starting sample (814802-05-A, prepared in Example 1) and dissolve in 1.0~3.0 mL of the solvent in Table 15, filter the filtrate and transfer to a 3 mL vial containing ~2 mg of mixed polymer, seal the vial containing the clear solution with a sealing film and prick several small holes on the film, place at room temperature and slowly volatilize, collect the obtained solid and carry out XRPD test. The test results are provided in Table 15. The crystal form A was obtained in all the polymer-induced crystallization tests.

TABLE 15

Summary of high polymer induction test

| Test No. | Solvent (v/v) | High polymer | Solid crystal form |
|---|---|---|---|
| 814802-14-A1 | MeOH | Mixed high polymer A | Crystal form A |
| 814802-14-A2 | DCM | | Crystal form A |
| 814802-14-A3 | $ACN/CHCl_3$ (1:1) | | Crystal form A |
| 814802-14-A4 | $CHCl_3$ | Mixed high polymer B | Crystal form A |
| 814802-14-A5 | acetone/DCM (1:2) | | Crystal form A |
| 814802-14-A6 | $EtOH/H_2O$ (1:1) | | Crystal form A |

Mixed high polymer A:
Polyvinylpyrrolidone, polyvinyl alcohol, polyvinyl chloride, polyvinyl acetate, hydroxypropyl methyl cellulose, and methyl cellulose (mixed in equal mass)
Mixed high polymer B:
Polycaprolactone, polyethylene glycol, polymethyl methacrylate, sodium alginate, and hydroxyethyl cellulose (mixed in equal mass)

Mixed high polymer A: Polyvinylpyrrolidone, polyvinyl alcohol, polyvinyl chloride, polyvinyl acetate, hydroxypropyl methyl cellulose, and methyl cellulose mixed in equal mass)

Mixed high polymer B: Polycaprolactone, polyethylene glycol, polymethyl methacrylate, sodium alginate, and hydroxyethyl cellulose (mixed in equal mass)

Example 10: Preparation of Crystal Form B of Compound X7 Hydrochloride

In this example, the preparation method of crystal form B of compound X7 hydrochloride comprises:

1. Weigh 199.8 mg of the starting sample (814802-05-A, prepared in Example 1) and add into a 20 mL vial, add 18.0 mL of water, and magnetically stir at 50° C. (~800 rpm) for about 1 day.
2. Filter (0.45 m PTFE filter head), slowly cool the filtrate to 5° C. at a rate of 0.1° C./min.
3. Separate the solid, and dry at room temperature and humidity.

Example 11: Preparation of Crystal Form C of Compound X7 Hydrochloride

In this example, the preparation method of crystal form C of compound X7 hydrochloride comprises:

1. Weigh 202.1 mg of the starting sample (814802-05-A, prepared in Example 1) and add into a 20 mL vial, add 18.0 mL of water, and magnetically stir at: 50° C. (~800 rpm) for about 3 h.
2. Filter (0.45 m PTFE filter head), slowly cool the filtrate to 5° C. at a rate of 0.1° C./min,
3. Separate the solid, and dry under vacuum at room temperature for 1 day.

Example 12: Preparation of Crystal Form D of Compound X7 Hydrochloride

In this example, crystal form C was obtained by heating the crystal form D of compound X7 hydrochloride, comprising:

1. Weigh 100.4 mg of crystal form C sample (814802-32-A2, prepared in Example 11) and add into a 20 mL vial.
2. Heat in a 160° C. oven for about 5 min.
3. Cool at room temperature.

Example 13: Preparation of Crystal Form F of Compound X7 Hydrochloride

In this example, the preparation method of crystal form F of compound X7 hydrochloride comprises:

1. Weigh 102.4 mg of the starting sample (814802-05-A, prepared in Example 1) and add into a 20 mL vial, and then add 14.0 mL of EtOH/$H_2O$ (5:2, v/v).
2. Sonicate for about 30 s and then filter (0.45 m PTFE filter head) and transfer the filtrate into another 20 mL vial
3. Keep the vial open at room temperature to volatilize.

The prepared crystal form A, B, C, D, E, and F of compound X7 were characterized by using XRPD, TGA, DSC, and $^1$H NMR, respectively.

(1) Characterization Results of Crystal Form A

Figure 2A:
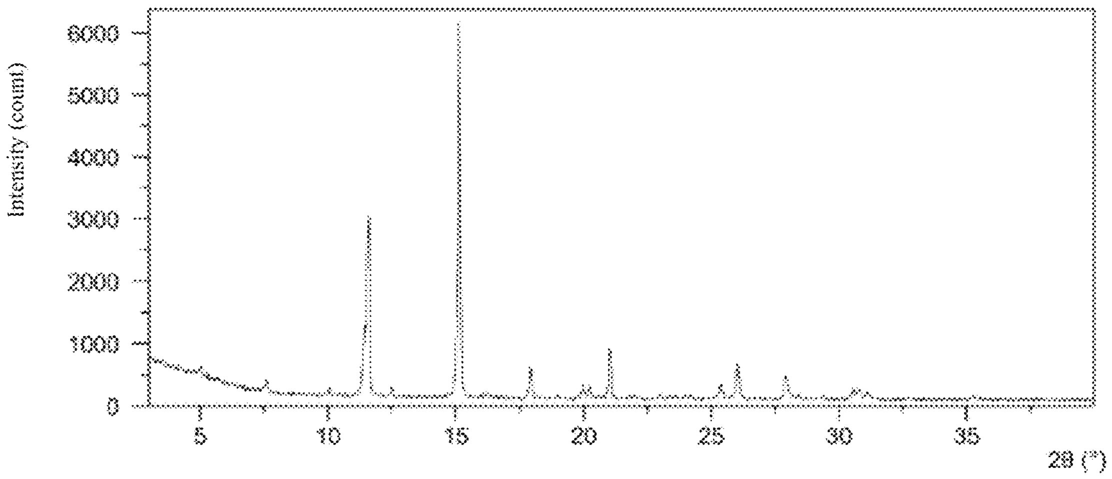
FIG. 2*a* is the XRPD diagram of crystal form A.

The XRPD characterization results of crystal form A (814802-11-A17, prepared in Example 6) are shown in FIG. 2*a*. The test results revealed that the XRPD characterization results of crystal form A prepared in other examples were consistent with the results depicted in FIG. 2*a*. The XRPD diffraction peak data of crystal form A are shown in Table 16.

TABLE 16

| XRPD diffraction peak data of crystal form A | | |
|---|---|---|
| 2θ | d interval | Strength, % |
| 7.57 | 11.69 | 1.98 |
| 9.99 | 8.85 | 0.99 |
| 11.57 | 7.65 | 48.37 |
| 12.49 | 7.09 | 2.66 |
| 15.12 | 5.86 | 100.00 |
| 17.92 | 4.95 | 8.12 |
| 19.96 | 4.45 | 3.32 |
| 21.03 | 4.22 | 13.00 |
| 25.34 | 3.51 | 3.97 |
| 26.01 | 3.43 | 9.83 |
| 27.89 | 3.20 | 5.94 |
| 30.64 | 2.92 | 2.02 |
| 31.11 | 2.87 | 1.75 |

In the selection of characteristic peaks of crystal form A, the primary characteristic peaks were at 15.12±0.2°, 11.57±0.2°, and 21.03±0.2°; the secondary characteristic peaks were at 26.01±0.2°, 17.92±0.2°, and 27.89±0.2°.

Figure 2B:
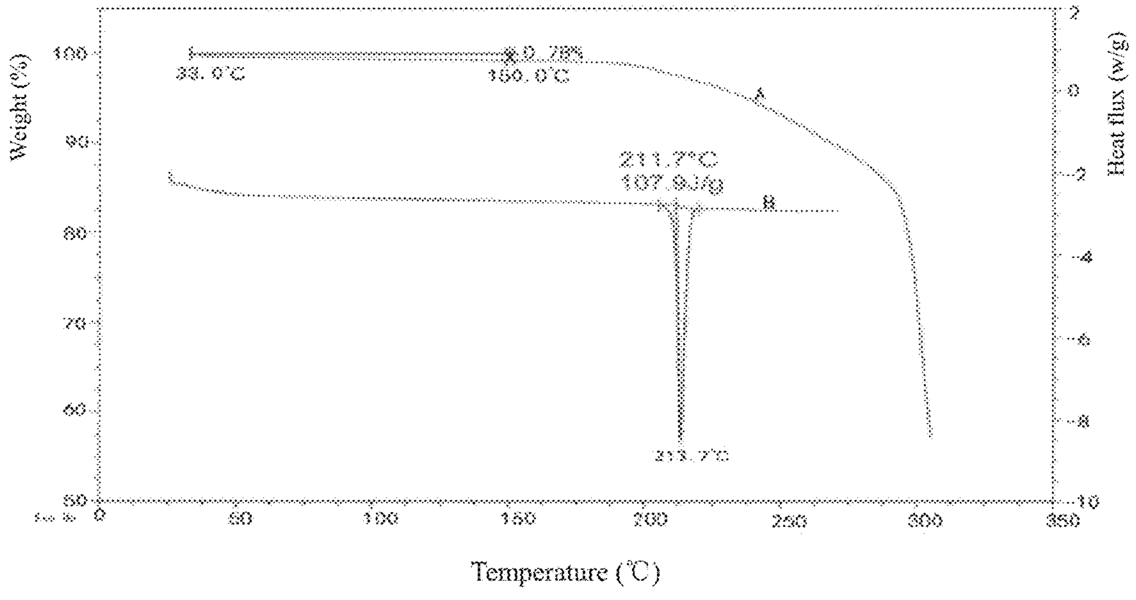
FIG. 2*b* is the TGA/DSC diagram of crystal form A; wherein, A curve illustrates the TGA diagram of crystal form A, and B curve diagram illustrates the DSC diagram of crystal form A.
Figure 2C:
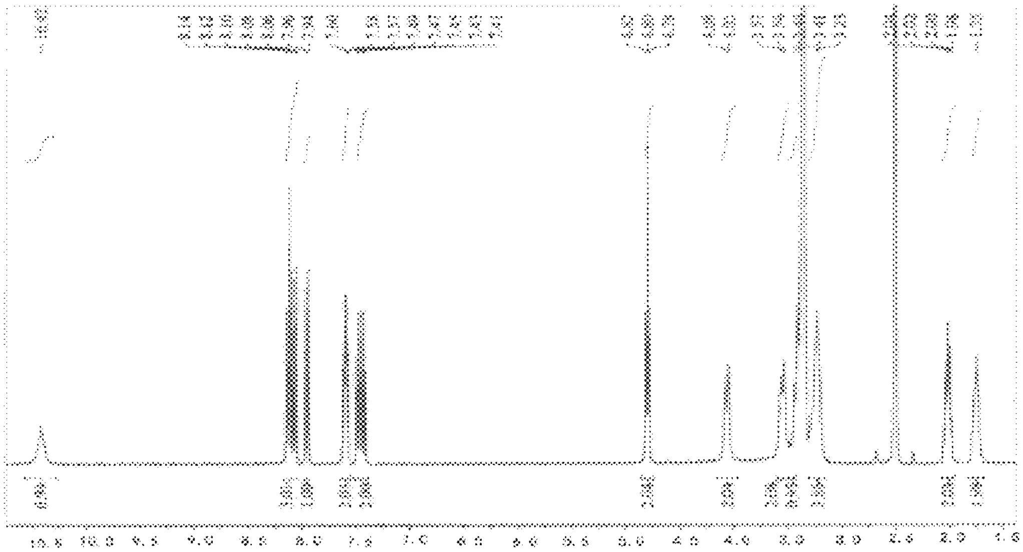
FIG. 2*c* is the $^1$H NMR diagram of crystal form A.
Figure 3A:
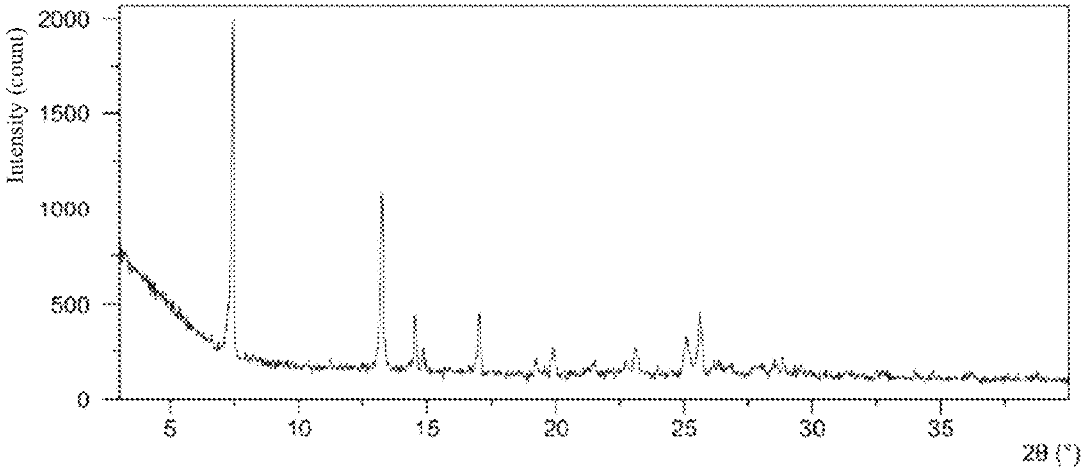
FIG. 3*a* is the XRPD diagram of crystal form B.

The TGA/DSC characterization results of crystal form A (814802-11-A17, prepared in Example 6) are shown in FIG. 2*b*. The test results revealed that the TGA/DSC characterization results of crystal form A prepared in other examples were consistent with the results depicted in FIG. 2*b*. The crystal form A sample lost 0.8% weight after heating to 150° C. and had a sharp endothermic peak at 211.7° C. (initial temperature). The $^1$HNMR characterization results of crystal form A (814802-11-A17, prepared in Example 6) are shown in FIG. 2*c*. The test results revealed that the $^1$HNMR characterization results of crystal form A prepared in other examples were consistent with the results depicted in FIG. 2*c*. It is speculated that crystal form A is an anhydrous crystal form according to the smaller weight loss in TGA and the single endothermic peak, (2) Characterization Results of Crystal Form B The XRPD characterization results of crystal form B (814802-09-A9, prepared in Example 4) are shown in FIG. 3*a*. The test results revealed that the XRPD characterization results of crystal form B prepared in other examples were consistent with the results depicted in FIG. 3*a*. The XRPD diffraction peak data of crystal form B are shown in Table 17.

TABLE 17

| XRPD diffraction peak data of crystal form B | | |
|---|---|---|
| 2θ | d interval | Strength, % |
| 7.38 | 11.98 | 100.00 |
| 13.19 | 6.71 | 58.50 |
| 14.48 | 6.12 | 15.71 |
| 16.99 | 5.22 | 19.95 |
| 19.86 | 4.47 | 9.05 |
| 21.38 | 4.16 | 3.03 |
| 23.08 | 3.85 | 8.18 |
| 25.05 | 3.55 | 11.35 |
| 25.57 | 3.48 | 19.60 |

In the selection of characteristic peaks of crystal form B, the primary characteristic peaks were at 738±0.20, 13.19±0.2°, and 16.99±0.2°. The secondary characteristic peaks were at 25.57±0.2°, 14.48±0.2°, and 25.05±0.2°.

Figure 3B:
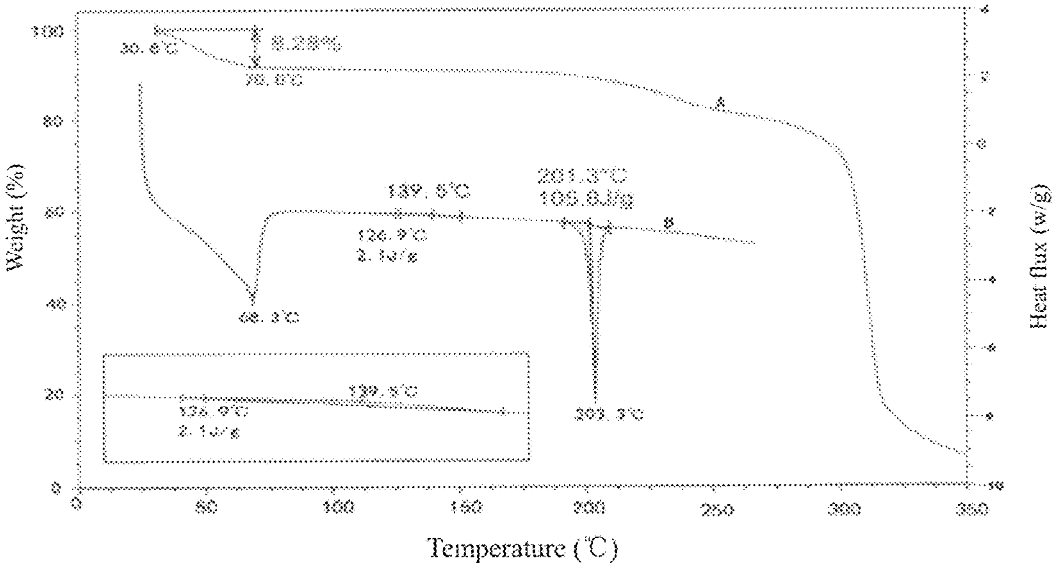
FIG. 3*b* is the TGA/DSC diagram of crystal form B; wherein, A curve illustrates the TGA diagram of crystal form B, and B curve diagram illustrates the DSC diagram of crystal form B.
Figure 3C:
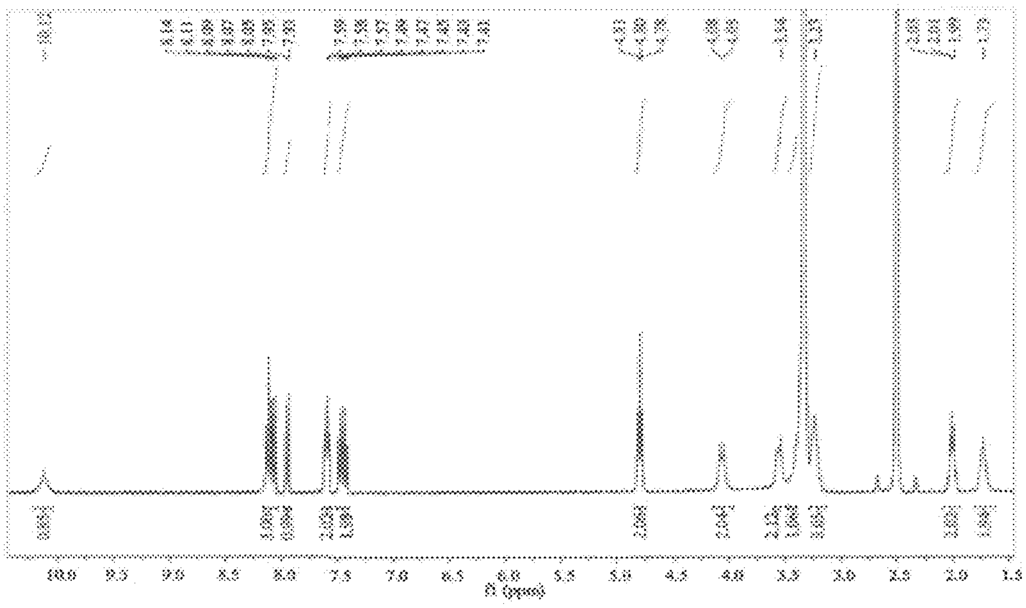
FIG. 3*c* is the $^1$H NMR diagram of crystal form B.

The TGA/DSC characterization results of crystal form B (814802-09-A9, prepared in Example 4) are shown in FIG. 3*b*. The test results revealed that the TGA/DSC characterization results of crystal form B prepared in other examples were consistent with the results depicted in FIG. 3*b*. TGA results showed that the sample lost 8.3% weight after heating to 70° C., DSC results showed two endothermic peaks at 68.3° C. (peak value) and 201.3° C. (initial), and a weak exothermic peak at 126.9° C. (initial). The $^1$HNMR characterization results of crystal form B (814802-09-A9, prepared in Example 4) showed (as shown in FIG. 3*c*) no solvent ACN residue in the crystal form B sample. The test results revealed that the $^1$HNMR characterization results of crystal form B prepared in other examples were consistent with the results depicted in FIG. 3*c*. Combined with the $^1$HNMR results, it is speculated that crystal form B is a hydrate, which transformed into anhydrous crystal form after heating for dehydration.

(3) Characterization Results of Crystal Form C

Figure 4A:
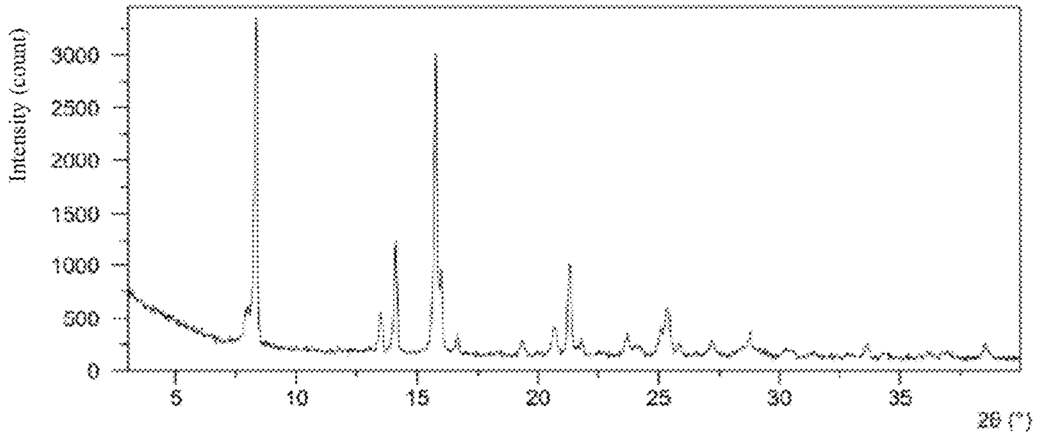
FIG. 4*a* is the XRPD diagram of crystal form C.

The XRPD characterization results of crystal form C (prepared in Example 11) are shown in FIG. 4*a*. The test results revealed that the XRPD characterization results of crystal form C prepared in other examples were consistent with the results depicted in FIG. 4*a*. The XRPD diffraction peak data of crystal form C are shown in Table 18.

TABLE 18

| XRPD diffraction peak data of crystal form C | | |
|---|---|---|
| 2theta | d interval | Strength, % |
| 8.26 | 10.71 | 100.00 |
| 13.43 | 6.59 | 11.43 |
| 14.03 | 6.31 | 33.63 |
| 15.68 | 5.65 | 90.14 |
| 15.91 | 5.57 | 25.61 |
| 16.59 | 5.34 | 5.72 |
| 19.28 | 4.60 | 4.57 |
| 20.59 | 4.31 | 8.64 |
| 21.25 | 4.18 | 28.11 |
| 21.73 | 4.09 | 4.77 |
| 23.64 | 3.76 | 6.87 |
| 25.30 | 3.52 | 14.35 |
| 25.78 | 3.46 | 3.39 |
| 27.13 | 3.29 | 4.22 |
| 28.70 | 3.11 | 6.84 |
| 30.31 | 2.95 | 1.69 |
| 33.57 | 2.67 | 3.45 |
| 34.30 | 2.61 | 1.31 |
| 38.46 | 2.34 | 3.91 |

In the selection of characteristic peaks of crystal form C, the primary characteristic peaks were at 8.26±0.2°, 15.68±0.2°, and 14.03±0.2°. The secondary characteristic peaks were at 21.25±0.2°, 25.30±0.2°, and 13.43±0.2°.

Figure 4B:
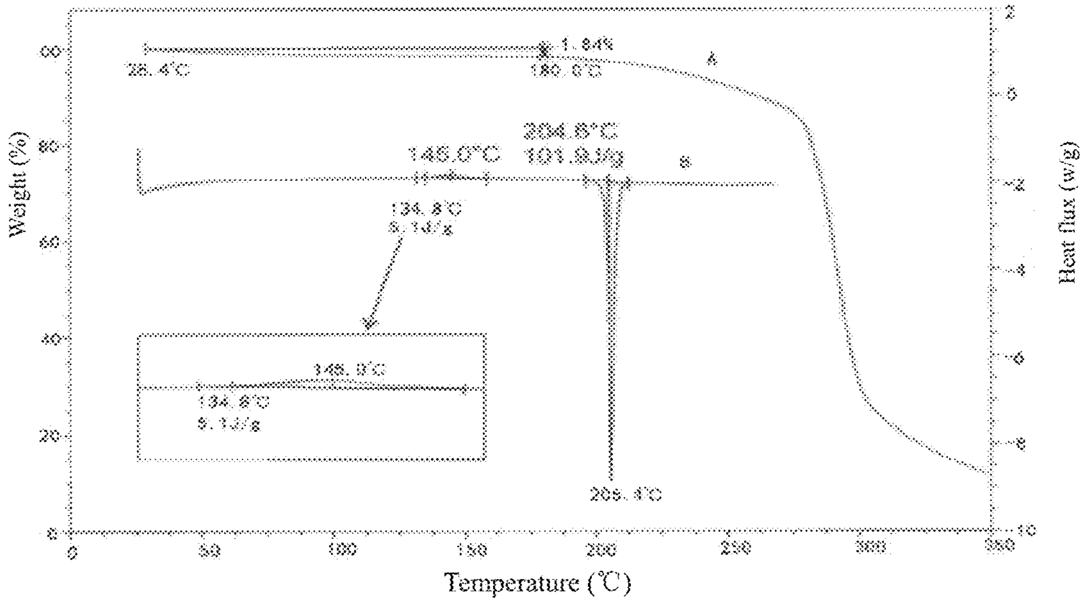
FIG. 4*b* is the TGA/DSC; diagram of crystal form C: wherein, A curve illustrates the TGA diagram of crystal form C, and B curve diagram illustrates the DSC diagram of crystal form C.

The TGA/DSC characterization results of crystal form C (prepared in Example 11) are shown in FIG. 4b. The test results revealed that the TGA/DSC characterization results of crystal form C prepared in other examples were consistent with the results depicted in FIG. 4b. The crystal form C lost 1.8% weight after heating to 180° C. and had an exothermic peak at 134.8° C. (initial) and a sharp endothermic peak at 204.6° C. (initial). Crystal form C had a relatively gentle weight loss and a single sharp endothermic peak, and it is speculated that crystal form C is an anhydrous crystal form.

(4) Characterization Results of Crystal Form D

Figure 5A:
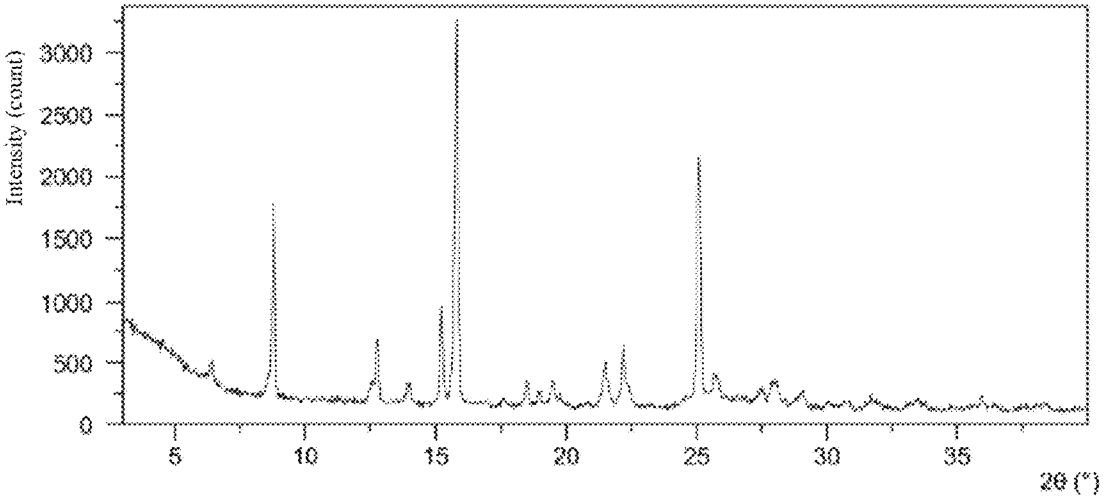
FIG. 5*a* is the XRPD diagram of crystal form D.

The XRPD characterization results of crystal form D (prepared in Example 12) are shown in FIG. 5a. The test results revealed that the TGA/DSC characterization results of crystal form D prepared in other examples were consistent with the results depicted in FIG. 5a. The XRPD diffraction peak data of crystal form D are shown in Table 19.

TABLE 19

| XRPD diffraction peak data of crystal form D | | |
|---|---|---|
| 2θ | d interval | Strength, % |
| 6.28 | 14.08 | 5.12 |
| 8.69 | 10.17 | 49.97 |
| 12.67 | 6.99 | 16.49 |
| 13.85 | 6.39 | 4.99 |
| 15.12 | 5.86 | 25.63 |
| 15.69 | 5.65 | 100.00 |
| 18.38 | 4.83 | 6.07 |
| 18.88 | 4.70 | 3.60 |
| 19.39 | 4.58 | 6.83 |
| 21.40 | 4.15 | 11.14 |
| 22.11 | 4.02 | 15.40 |
| 24.98 | 3.56 | 63.49 |
| 25.62 | 3.48 | 8.36 |
| 27.39 | 3.26 | 4.96 |
| 27.89 | 3.20 | 6.90 |
| 28.94 | 3.08 | 3.90 |
| 30.65 | 2.92 | 1.77 |
| 31.68 | 2.82 | 2.18 |
| 33.36 | 2.69 | 2.32 |
| 35.84 | 2.51 | 3.22 |

In the selection of characteristic peaks of crystal form 1.), the primary characteristic peaks were at 15.69±0.2°, 24.98±0.2°, and 8.69±0.2°. The secondary characteristic peaks were al: 15.12±0.2°, 12.67±0.2°, and 22.11±0.2°.

Figure 5B:
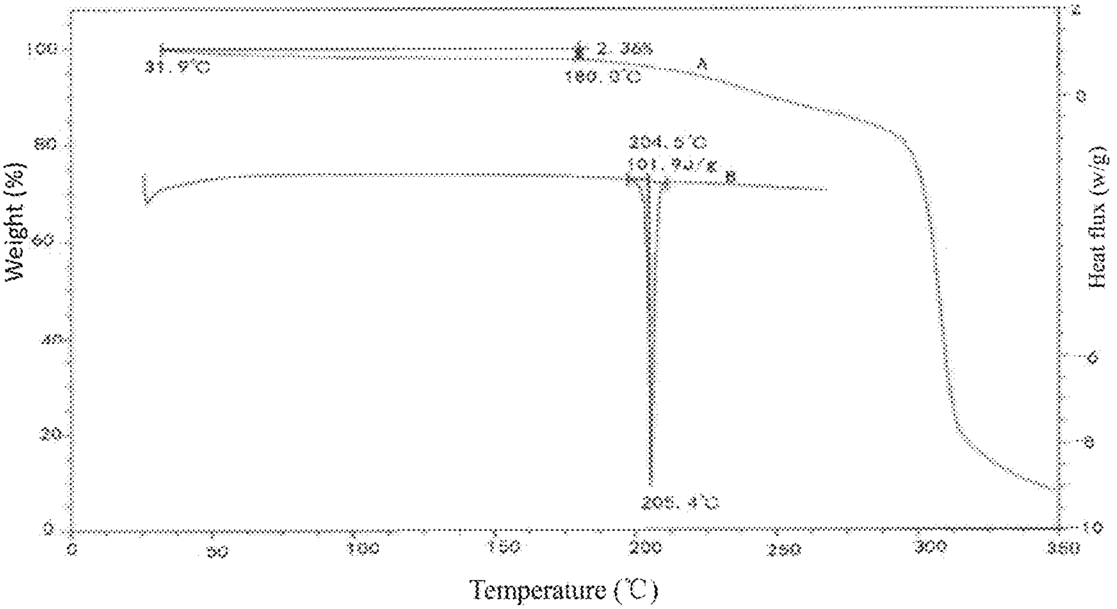
FIG. 5*b* is the TGA/DSC diagram of crystal form D; wherein, A curve illustrates the TGA diagram of crystal form D, and B curve diagram illustrates the DSC diagram of crystal form D.

The TGA/DSC characterization results of crystal form D (prepared in Example 12) are shown in FIG. 5b. The test results revealed that the TGA/DSC characterization results of crystal form D prepared in other examples were consistent with the results depicted in FIG. 5b. The crystal form D lost 2.4% weight after heating to 180° C. and had a sharp endothermic peak at 204.5° C. (initial). It is speculated that crystal form D is an anhydrous crystal form according to the relatively gentle weight loss in TGA and the single endothermic peak in DSC.

(5) Characterization Results of Crystal Form E

Figure 6:
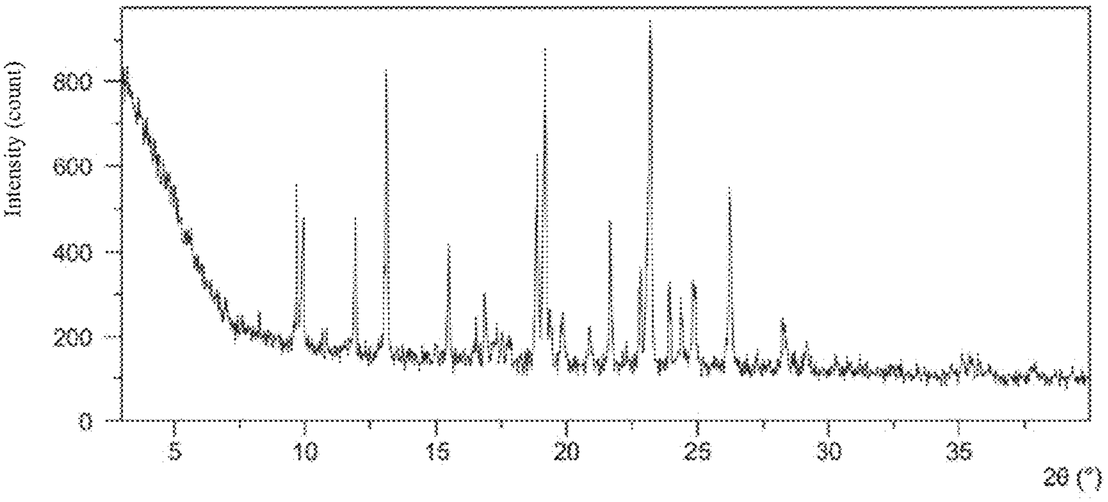
FIG. 6 is the XRPD diagram of crystal form E.

The XRPD characterization results of crystal form E (814802-10-A5, prepared in Example 5) are shown in FIG. 6. The test results revealed that the TGA/DSC characterization results of crystal form E prepared in other examples were consistent with the results depicted in FIG. 6. The XRPD diffraction peak data of crystal form E are shown in Table 20.

TABLE 20

| XRPD diffraction peak data of crystal form E | | |
|---|---|---|
| 2θ | d interval | Strength, % |
| 9.57 | 9.24 | 40.00 |
| 9.81 | 9.02 | 33.15 |
| 11.81 | 7.50 | 35.10 |
| 13.01 | 6.80 | 83.29 |
| 15.36 | 5.77 | 29.03 |
| 16.40 | 5.41 | 7.38 |
| 16.76 | 5.29 | 19.14 |
| 18.75 | 4.73 | 60.18 |
| 19.05 | 4.66 | 87.86 |
| 19.72 | 4.50 | 11.93 |
| 20.77 | 4.28 | 9.96 |
| 21.56 | 4.12 | 35.94 |
| 22.71 | 3.92 | 26.29 |
| 23.08 | 3.85 | 100.00 |
| 23.83 | 3.73 | 24.60 |
| 24.28 | 3.67 | 19.51 |
| 24.75 | 3.60 | 21.74 |
| 26.12 | 3.41 | 52.84 |
| 28.19 | 3.17 | 12.12 |

In the selection of characteristic peaks of crystal form E, the primary characteristic peaks were at 23.08±0.2°, 19.05±0.2°, and 13.01±0.2°. The secondary characteristic peaks were at 26.12±0.2°, 21.56±0.2°, and 11.81±0.2°. The tertiary characteristic peaks were at 15.36±0.2°, 23.83±0.2°, and 24.75±0.2°.

(6) Characterization Results of Crystal Form F

Figure 7A:
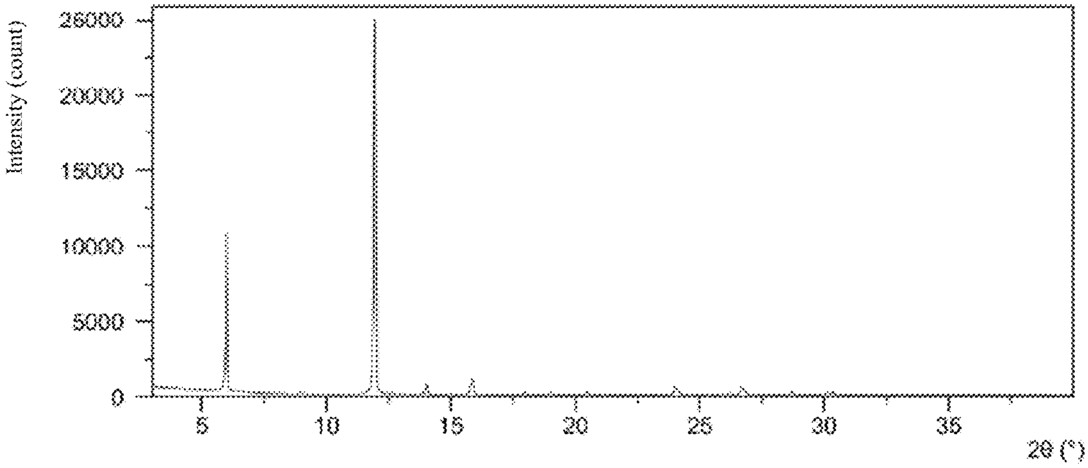
FIG. 7*a* is the XRPD diagram of crystal form F.

The XRPD characterization results of crystal form F (prepared in Example 13) are shown in FIG. 7a. The test results revealed that the TGA/DSC characterization results of crystal form F prepared in other examples were consistent with the results depicted in FIG. 7a. The XRPD diffraction peak data of crystal form F are shown in Table 21.

TABLE 21

| XRPD diffraction peak data of crystal form F | | |
|---|---|---|
| 2θ | d interval | Strength, % |
| 5.77 | 15.31 | 30.71 |
| 8.82 | 10.03 | 0.57 |
| 11.74 | 7.54 | 100.00 |
| 13.81 | 6.41 | 1.82 |
| 15.66 | 5.66 | 4.04 |
| 17.74 | 5.00 | 0.69 |
| 18.79 | 4.72 | 0.41 |
| 20.25 | 4.39 | 0.73 |
| 23.79 | 3.74 | 1.99 |
| 26.51 | 3.36 | 1.91 |
| 28.49 | 3.13 | 1.07 |
| 30.11 | 2.97 | 0.89 |
| 33.04 | 2.71 | 0.13 |

In the selection of characteristic peaks of crystal form F, the primary characteristic peaks were at 11.74±0.2°, 5.77±0.2°, and 15.66±0.2°.

Figure 7B:
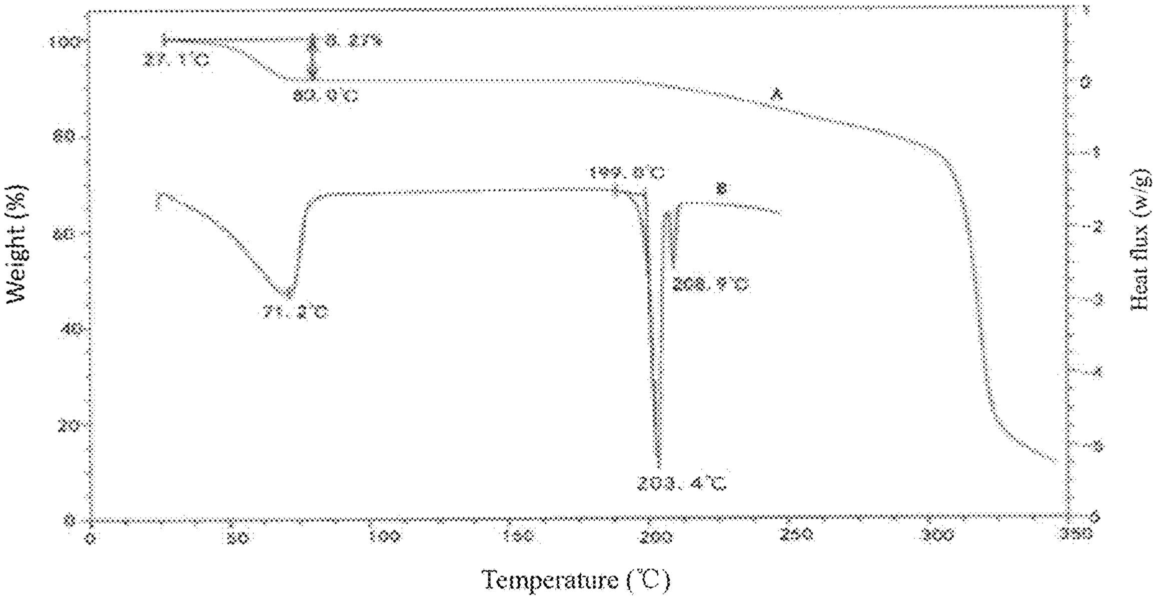
FIG. 7*b* is the TGA/DSC diagram of crystal form F; wherein, A curve illustrates the TGA diagram of crystal form F, and B curve diagram illustrates the DSC diagram of crystal form F.
Figure 7C:
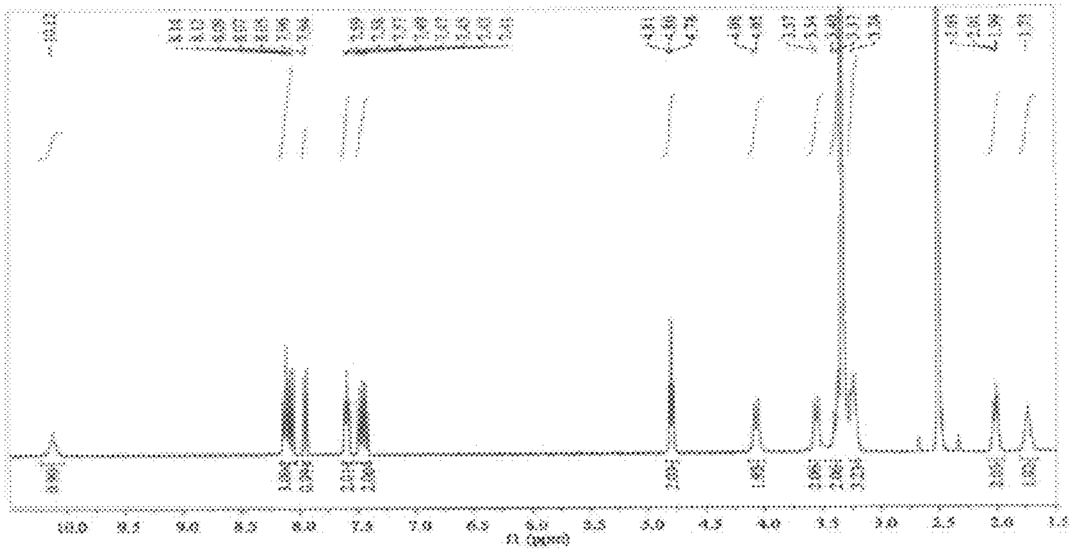
FIG. 7*c* is the $^1$H NMR diagram of crystal form F.

The TGA/DSC results of crystal form F (prepared in Example 13) are shown in FIG. 7b. The test results revealed that the TGA/DSC characterization results of crystal form F prepared in other examples were consistent with the results depicted in FIG. 7b. The crystal form F sample lost 8.3% weight after heating to 80° C., and had 3 endothermic peaks at 71.2° C., 203.4° C., and 208.9° C. (peak). The $^{1}$HNMR results of crystal form F (prepared in Example 13) showed (as shown in FIG. 7c) no solvent EtOH residue. The test results revealed that the $^{1}$HNMR characterization results of crystal form F prepared in other examples were consistent with the results depicted in FIG. 7*c*. Combined with $^1$HNMR results and TGA step weight loss, it is speculated that crystal form F is a hydrate.

Test case 1 Study on the transformation relationship between crystal forms

To further study the stability relationship between anhydrous crystal forms A, C, and D and hydrate crystal forms B and F, suspension competition tests between crystal forms were set up, including suspension competition of crystal forms A, C, and 1) in EtOH and $CHCl_3$ at room temperature and 50° C., and suspension test of crystal forms A, B, and F in acetone/$H_2O$ ($a_w$=0~1) at room temperature.

1.1 Suspension Competition of Anhydrous Crystal from A/C/D

To study the stability relationship of anhydrous crystal from A, C, and D at different temperatures and different solvent conditions, suspension competition tests in EtOH and $CHCl_3$ at room temperature and 50° C. were set up. Specific steps were as follows: 1) preparing the saturated solution of the starting sample (814802-05-A, prepared in Example 1) in different solvents at a certain temperature; 2) adding the same mass of crystal form A (814802-11-A17, prepared in Example 6), C (prepared in Example 11), and D sample (prepared in Example 12) (about 4 mg each) into 0.5 mL of saturated solution to develop suspension; 3) suspending and stirring at room temperature and 50° C. for about 2 days (~800 rpm); 4) separating the remaining solid (wet sample) and carrying out XRPD test (transmission). In all the tests, the initial mixed crystal form finally transformed into anhydrous crystal form A, indicating that crystal form A was more stable than crystal form C and D in the range of room temperature to 50° C.

1.2 Suspension Competition of Anhydrous Crystal From A and Hydrate B/F

To study the stability relationship between anhydrous crystal form A and hydrate crystal form B/F under different water activity conditions, the suspension competition test in acetone/$H_2O$ solvent system with different water activity was set up at room temperature. Specific steps are as follows: 1) prepare 0.5 mL each of the saturated solutions of the starting sample (814802-05-A, prepared in Example 1) in different solvents at room temperature; 2) add the same mass of crystal form A (814802-11-A17, prepared in Example 6), B (814802-09-A9, prepared in Example 4), and F sample (prepared in Example 13) (about 5 mg each) into the saturated solution to develop suspension, and magnetically stir at room temperature for about 2 days (~800 rpm)[2]; 3) separate the remaining solid and carry out XRPD test (transmission). The results showed that when the water activity $a_w$ was ≤0.8, the initial mixed crystal form eventually transformed into anhydrous crystal form A; after suspending and stirring in $H_2O$ ($a_w$=1), the initial mixed crystal form finally transformed into hydrate crystal form B. The above results showed that the anhydrous crystal form A was more stable at room temperature and water activity $a_w$=0~0.8, and hydrate crystal form B was more stable at $a_w$=1.

Test Case 2 Crystal Form Evaluation

Combined with the test results of suspension competition in test case 1, crystal form A had the highest thermodynamic stability among the 3 anhydrous crystal forms; hydrate crystal form B had better stability than other crystal forms at $a_w$=1. Therefore, crystal form A and crystal form B were selected for further assessment, including equilibrium solubility in water, solid state stability, hygroscopicity, and PLM morphology.

2.1 Equilibrium Solubility in Water

The equilibrium solubility in water was tested at room temperature for crystal form A sample (814802-11-A17, prepared in Example 6) and crystal form B sample (814802-09-A9, prepared in Example 4). As a comparison, the equilibrium solubility was also tested under the same conditions for crystal form C sample (prepared in Example 11), crystal form D sample (prepared in Example 12), and crystal form F sample (prepared in Example 13). The suspension of each crystal form (~10 mg/mL) was prepared in the test, magnetically stirred at room temperature for 24 hours (rotating speed~800 rpm) and then centrifuged (10000 rpm, 5 min). The solubility and pH were determined for the supernatant after filtration (0.22 μM PTFE filter membrane) and XRPD (transmission) for the solid. The test results are summarized in Table 22. The crystal forms of crystal form A and B remained unchanged before and after the test, and the 24-hour solubility in water was 3.8 and 3.4 mg/mL, respectively. After 24 hours of equilibrium in water, the crystal forms C, 0, and F were all transformed into crystal form B.

TABLE 22

Summary of results of equilibrium solubility in water for crystal form A/B/C/D/F

| Starting crystal form (serial number) | Solubility (mg/mL) | pH | Crystal form transformation |
|---|---|---|---|
| Crystal form A | 3.8 | 4.6 | No |
| Crystal form B | 3.4 | 4.9 | No |
| Crystal form C | 3.3 | 4.9 | Transformed into crystal form B |
| Crystal form D | 3.1 | 4.9 | Transformed into crystal form B |
| Crystal form F | 2.9 | 4.7 | Transformed into crystal form B |

2.2 Solid-State Stability

To assess the solid-state stability of crystal form A (814802-11-A17, prepared in Example 6) and hydrate crystal form B (814802-09-A9, prepared in Example 4), a proper amount of samples were weighed and placed in a sealed container for one day at 80° C. and in an open container at 25° C./60% RH and 40° C./75% RH for one week. For the solid samples separated under different conditions, the chemical stability was evaluated by determining purity using the HPLC method, and the physical stability was evaluated by determining the crystal form using the XRPD test. The evaluation results are summarized in Table 23. Under three test conditions, crystal form A had no crystal form transformation or reduction of HPLC purity, indicating that crystal form A had good physical and chemical stability. Crystal form B had no change in crystal form or HPLC purity after being placed at 25° C./60% RH for one week.

2.3 Hygroscopicity

Figure 8A:
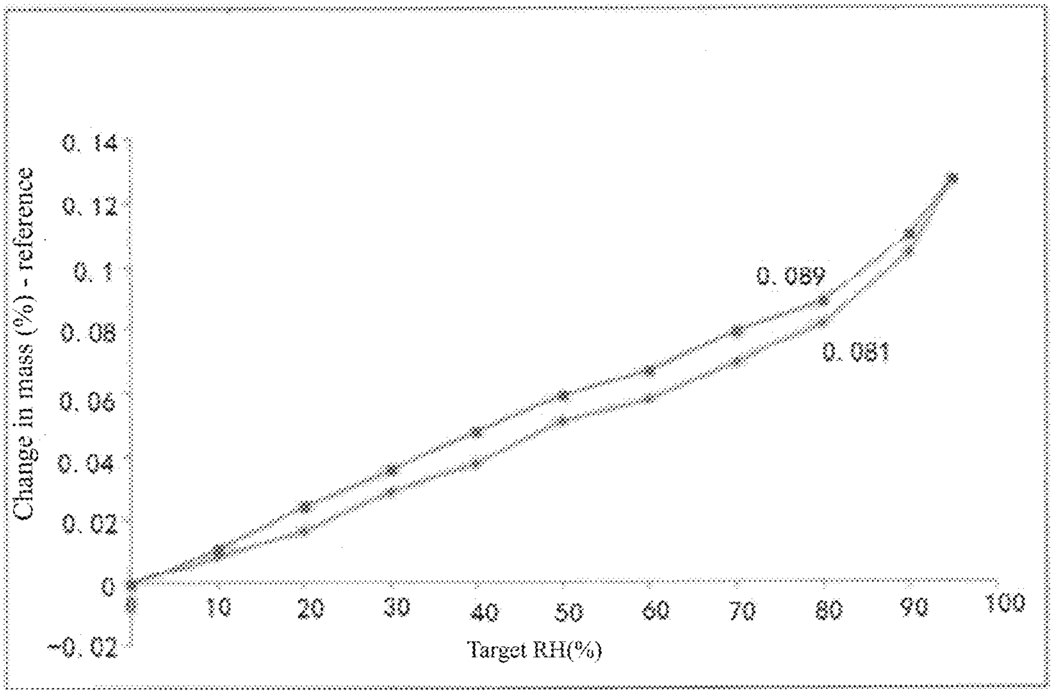
FIG. 8*a* is the DVS diagram of crystal form A; wherein, ( ) represents cycle 1 adsorption, and ( ) represents cycle 1 desorption.
Figure 8B:
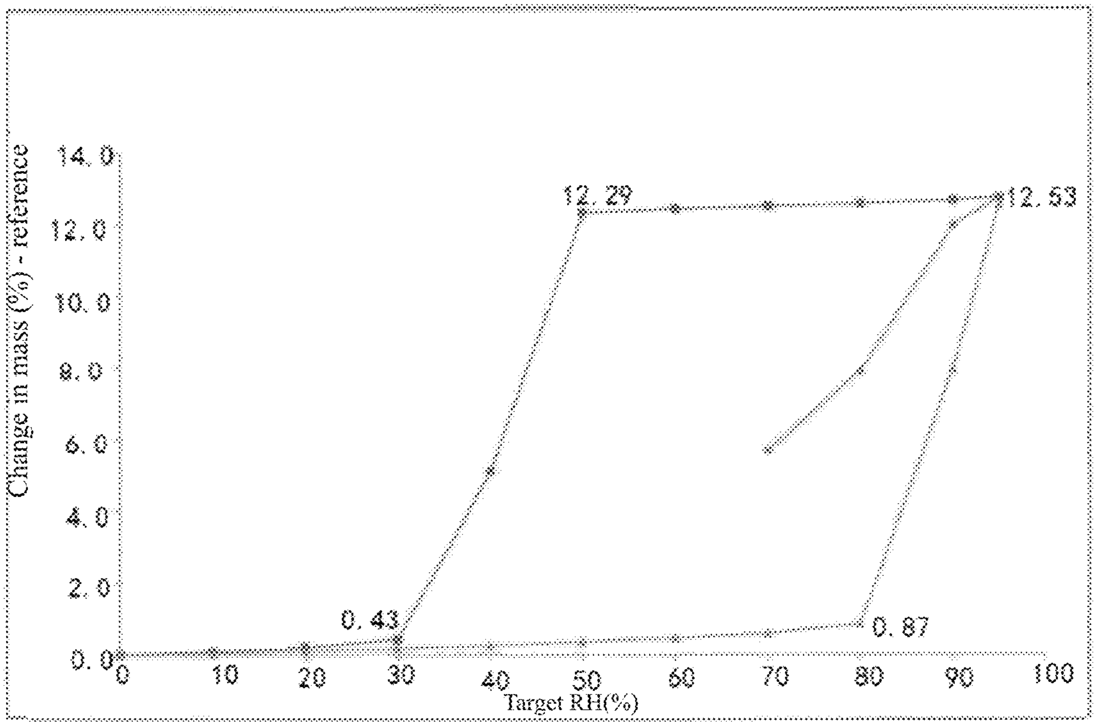
FIG. 8*b* is the DVS diagram of crystal form B; wherein, ( ) represents cycle 1 adsorption, ( ) represents cycle 1 desorption, and ( ) represents cycle 2 adsorption.

The hygroscopicity was evaluated using the dynamic moisture adsorption test at 25° C. for crystal form A sample (814802-11-A17, prepared in Example 6) and crystal form B sample (814802-09-A9, prepared in Example 4), and the results are shown in FIG. 8*a* and FIG. 8*b*.

Figure 9A:
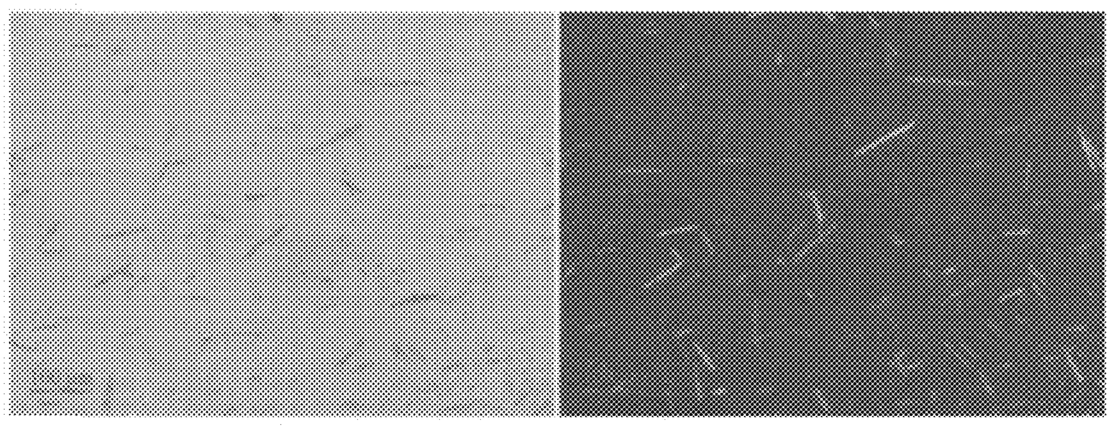
FIG. 9*a* is the PLM diagram of crystal form A.
Figure 9B:
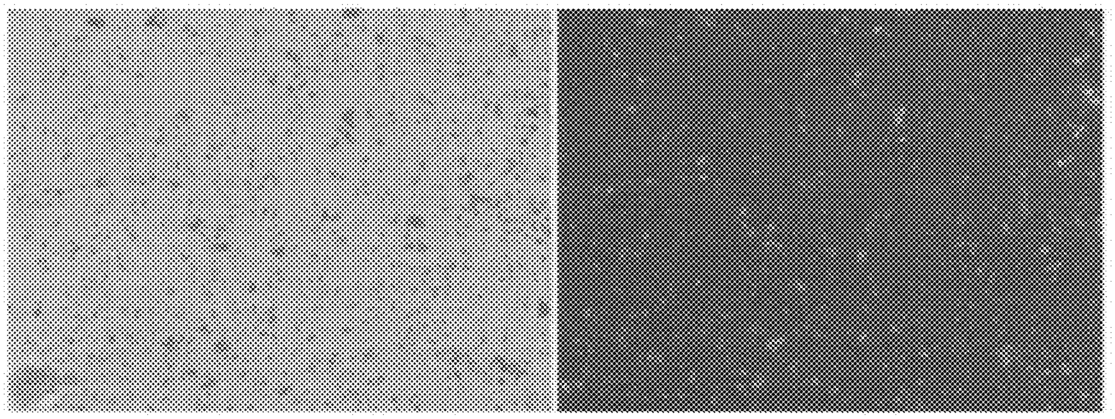
FIG. 9*b* is the PLM diagram of crystal form B.

Crystal form A sample absorbed 0.08% water at 25° C./80% RH indicating that crystal form A had no hygroscopicity, and had no crystal form transformation after the DVS test, In the desorption process, the crystal form B sample absorbed 12.3% water at 50% RH. The water absorption decreased rapidly when the relative humidity was reduced to 30% RH, and the crystal absorbed 0.4% water at 30% RH. It is speculated that the process led to transformation from hydrate to anhydrous crystal form. During the adsorption process, the water absorption increased rapidly when the relative humidity increased to 80% RH, and it was 12.5% at 95% RH. It is speculated that the anhydrous crystal form transformed into hydrate during this process. 2.4 PLM PLM test was carried out to evaluate the crystal morphology for crystal form A sample (814802-11-A17, prepared in Example 6) and crystal form B sample (814802-09-A9, prepared in Example 4), and the results are shown in FIG. 9*a* and FIG. 9*b*. Crystal form A is an acicular crystal, and crystal form B is a granular crystal with particle size <20 μm.

Test Case 3 Activity Test of Crystal Form A as a Vasodilator (1) Preparation of Rabbit Vascular Smooth Muscle Specimen In Vitro After anesthetizing the rabbit, its chest was quickly cut open. The descending aorta, connective tissues, and surrounding adipose tissues were removed (if the serotonin receptor antagonistic test was carried out, a smooth stainless steel rod was used to remove the endothelial cells), and the aorta was cut into 3-5 mm vascular rings. Then, the steel wire hook was passed through the vascular ring, with one end fixed on the ventilation hook and the other end connected to the tension transducer and placed in a bath tube containing 20 ml of nutrient solution. The change in tension was recorded. The temperature was maintained in the bath tube at 37±0.5° C., and a mixed gas (95% $O_2$+5% $CO_2$) was introduced at the rate of 1-2 bubbles per second. The initial load of the specimen was 1.5 g. The nutrient solution was changed every 20 min, balanced for 2 h, and the test was started after the baseline became stable.

(2) Relaxation effect: of Crystal Form A (814802-11-A17, Prepared in Example 6) on Isolated Rabbit Vascular Smooth Muscle Contraction Induced by Spasmodic Agent AD After the specimen tension became stable, a waveform was recorded, the spasmodic agent adrenaline hydrochloride (AD) ($10^{-5}$ mol/L) was added in the bath tube to induce contraction. After achieving the maximum contraction, the specimen was sufficiently rinsed, the K-H solution was changed every 20 min, balanced for 60 min, and then, the spasmodic agent was again used at the same concentration to induce contraction after the baseline became stable. When the maximum response of the next contraction was basically the same as that of the previous one, the prepared X7 solution ($1\times10^{-9}$~$1\times10^{-6}$ mol/L) was added, and the waveform recorded. With the maximum relaxation response of X7 as 100%, the relaxation percentage of X7 at each concentration was calculated and the dose-effect curve plotted using the relaxation percentage of X7 as the vertical coordinate and the logarithm of each concentration as the horizontal coordinate. X7 had a relaxation effect on the specimen contraction caused by spasmodic agent AD, and its relaxation effect on adrenaline showed a certain dose dependence. The $-\log EC_{50}$ value of the drug to relax the rabbit aorta contraction by AD was 8.07±0.09.

(3) Antagonistic Effect of Crystal form A (81480241-A17, Prepared in Example 6) on 5-hydroxytryptamine (5-HT) Receptor in Rabbit Vascular Smooth Muscle After the specimen tension became stable, the waveform was recorded and 5-HT added cumulatively in the bath tube ($10^{-7}$~$3\times10^{-4}$ mol/L) until reaching the maximum response, and the waveform was recorded again. Then, K-H solution was used to repeatedly flush the specimen, it was balanced for 1.5 h, 5-HT ($10^{-7}$ mol/L) was added, and 5-HT was added again using the same method 20 min later. The dose-effect curve was plotted with the maximum response as 100%, the percentage of 5-HT contraction as the vertical ordinate, and the negative logarithm of each 5-HT concentration as the horizontal ordinate. After adding drug X7 ($10^{-7}$ mol/L), the dose-effect curve of 5-HT shifted significantly parallel to the right, but the maximum response was almost unchanged. The statistical analysis of the percentage of response al: each concentration showed significant difference (P<0.01). The $PA_2$ value of the drug to resist rabbit aorta contraction by 5HT was 8.86±0.14.

(4) Effect of Positive Control Dreg Sarpogrelate on Dose-Effect Curve of 5HT Cumulative Contraction After the specimen tension became stable, a waveform was recorded and 5-HT cumulatively added in the bath tube ($10^{-7}$~$3\times10^{-4}$ mol/L) until reaching the maximum response, and the waveform was recorded again. Then, the K-H solution was used to repeatedly flush the specimen, it was balanced for 1.5 h, sarpogrelate ($10^{-6}$ mol/L) was added, and 5-HT was added again using the same method 20 min later. The dose-effect curve was plotted with the maximum response as 100%, the percentage of 5-HT contraction as the vertical ordinate, and the negative logarithm of each 5-HT concentration as the horizontal ordinate. After adding drug sarpogrelate ($10^{-6}$ mol/L), the dose-effect curve of 5-HT shifted significantly parallel to the right, but the maximum response was almost unchanged. The statistical test on the percentage of response at each concentration showed significant difference (P<0.01). The $PA_2$ value of the drug to resist rabbit aorta contraction by 5-HT was 7.21±0.08.

(5) Antagonistic Effect of Crystal Form A (814802-11-A17, Prepared in Example 6) on α Receptor in Rabbit Vascular Smooth Muscle After the specimen tension became stable, a waveform was recorded and norepinephrine added cumulatively in the bath tube ($10^{-8}$~$6\times10^{-5}$ mol/L) until reaching the maximum response, and then, the waveform was recorded again. Then, K-H solution was used to repeatedly flush the specimen, it was balanced for 1 h, X7 ($3\times10^{-8}$ mol/L) was added, and phenylephrine was added again using the same method 20 min later. The dose-effect curve was plotted with the maximum response as 100%, the percentage of phenylephrine contraction as the vertical ordinate, and the negative logarithm of each phenylephrine concentration as the horizontal ordinate. After adding drug X7 ($3\times10^{-8}$ mol/L), the dose-effect curve of norepinephrine shifted significantly parallel to the right, but the maximum response was almost unchanged. The statistical t test on the percentage of response at each concentration showed significant difference (most P values<0.01). The $PA_2$ value of the drug to resist rabbit aorta contraction by norepinephrine was 7.98±0.04.

(6) Effect of Positive Control Drug Doxazosin on Dose-Effect Curve of Norepinephrine Cumulative Contraction After the specimen tension became stable, a waveform was recorded and norepinephrine added cumulatively in the bath tube ($10^{-8}$~$3\times10^{-3}$ mol/L) until reaching the maximum response, and then, the waveform was recorded. Then, K-H solution was used to repeatedly flush the specimen, the K-H solution was changed every 20 min, and it was balanced for 60 min. After baseline returned to the stable level, doxazosin ($10^{-7}$ mol/L) was added, and then noradrenalin ($10^{-6}$~$10^{-2}$ mol/L) was added using the same method 15 min later. The dose-effect curve was plotted with the maximum response as 100%, the percentage of noradrenalin contraction as the vertical ordinate, and the negative logarithm of each phenylephrine concentration as the horizontal ordinate. After adding doxazosin ($10^{-7}$ mol/L), the dose-effect curve of phenylephrine shifted significantly parallel to the right, but the maximum response was almost unchanged. The statistical test on the percentage of response at each concentration showed significant difference (most P values <0.01). The $PA_2$ value of the positive control drug doxazosin to resist rabbit aorta contraction by NA was 7.83±0.05.

Test Case 4 Dissolution Test Data of Crystal Form A in the Solid Preparation

X7 is stable under various pH conditions and high temperature, and is suitable for developing gastric soluble preparations. In this test case, the dissolution test data of crystal form A (814802-11-A17, prepared in Example 6) for preparing tablets using conventional preparation method are as follows.

(1) Dissolution Conditions:

Dissolution medium: 1000 ml of water, ph1.0 hydrochloric acid solution, pH4.5 acetate buffer solution, and pH6.8 phosphate buffer solution were used as the dissolution medium.

Method: Method 2. Determination of dissolution and release, general notice 0931, volume 4, China Pharmacopoeia 2015

Rotation rate: 50 r/min

Temperature: 37° C.

Sampling point: sample the dissolution solution at: 5, 10, 15, 20, 30, 45, and 60 min, pass through 0.45 μm organic filter membrane, collect the subsequent filtrate, and directly inject and test in the high-performance liquid chromatograph.

Determination method: HPLC, general notice 0512, volume 4, China Pharmacopoeia 2015.

(2) Test Results:

TABLE 23

Dissolution curve of X7 in pH 1.0 hydrochloric acid (n = 12)

| Dissolution medium | Batch No. | Dissolution (%) 5 min | 10 min | 15 min | 20 min | 30 min | 45 min | 60 min |
|---|---|---|---|---|---|---|---|---|
| pH 1.0 hydrochloric acid solution | 1 | 56.35 | 79.77 | 87.18 | 90.35 | 92.67 | 93.80 | 94.85 |
| | 2 | 53.38 | 80.07 | 87.91 | 90.71 | 92.36 | 94.64 | 95.59 |
| | 3 | 47.02 | 69.44 | 78.11 | 82.13 | 85.67 | 88.04 | 89.38 |

TABLE 24

Dissolution curve of X7 in water (n = 12)

| Dissolution medium | Batch No. | Dissolution (%) 5 min | 10 min | 15 min | 20 min | 30 min | 45 min | 60 min |
|---|---|---|---|---|---|---|---|---|
| Water | 1 | 66.56 | 82.94 | 87.03 | 89.19 | 91.59 | 92.74 | 95.50 |
| | 2 | 69.38 | 81.65 | 87.52 | 89.28 | 90.23 | 93.71 | 94.79 |
| | 3 | 55.81 | 76.29 | 82.88 | 86.17 | 89.03 | 91.25 | 93.32 |

TABLE 25

Dissolution curve of X7 in pH 6.8 phosphate buffer (n = 12)

| Dissolution medium | Batch No. | Dissolution (%) 5 min | 10 min | 15 min | 20 min | 30 min | 45 min | 60 min |
|---|---|---|---|---|---|---|---|---|
| pH 6.8 phosphate buffer | 1 | 41.19 | 61.45 | 74.02 | 80.98 | 88.63 | 93.17 | 93.92 |
| | 2 | 37.44 | 57.94 | 71.44 | 78.18 | 85.90 | 91.18 | 92.61 |
| | 3 | 40.85 | 57.54 | 72.13 | 78.90 | 86.29 | 91.62 | 94.32 |

TABLE 26

Dissolution curve of X7 in pH 4.5 acetate buffer (n = 12)

| Dissolution medium | Batch No. | Dissolution (%) 5 min | 10 min | 15 min | 20 min | 30 min |
|---|---|---|---|---|---|---|
| pH 4.5 acetate buffer | 1 | 66.86 | 84.76 | 88.81 | 90.28 | 91.97 |
| | 2 | 69.82 | 84.57 | 88.29 | 89.80 | 91.49 |
| | 3 | 59.45 | 80.35 | 85.98 | 87.82 | 89.45 |

It can be seen from the dissolution curves of the 4 media that in this test case, the X7 preparation tablets prepared using crystal form A have to basically consistent dissolution behavior among the 3 batches. The self prepared samples have good inter-batch repeatability and uniform quality.

The invention claimed is:

1. A crystal of compound X7 hydrochloride, wherein the crystal comprises crystal form A and the 2θ diffraction angle of the X-ray powder diffraction diagram of crystal form A exhibits diffraction peaks at 15.12±0.2°, 11.57±0.2°, and 21.03±0.2°;

wherein the structural formula of the crystal of compound X7 hydrochloride is shown in formula (I):

Formula (I)

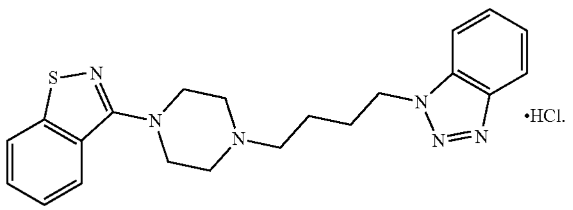

2. The crystal of compound X7 hydrochloride of claim 1, wherein a thermogravimetric analysis diagram of crystal form A exhibits a weight loss of 0.8±0.5% in the range of 30.0~155.0° C.

and/or a differential scanning calorimetry of crystal form A exhibits endothermic peaks in the range of 210.0~220.0° C.;

and/or the crystal form A is an anhydrous crystal form.

3. A pharmaceutical composition that comprises the crystal of compound X7 hydrochloride of claim 1 and a pharmaceutically acceptable carrier or excipient.

4. A method for treatment or delay of hypertension, comprising administering the crystal of compound X7 hydrochloride of claim 1 or a pharmaceutical composition comprising the crystal of compound X7 hydrochloride.

5. The crystal of compound X7 hydrochloride of claim 1, wherein the 2θ diffraction angle of the X-ray powder diffraction diagram of the crystal form A exhibits characteristic diffraction peaks at 26.01±0.2°, 17.92±0.2°, and 27.89±0.2°.

6. The crystal of compound X7 hydrochloride of claim 1, wherein the 2θ diffraction angle of the X-ray powder diffraction diagram of the crystal form A exhibits characteristic diffraction peaks at 25.34±0.2°, 19.96±0.2°, 12.49±0.2°, 30.64±0.2°, 7.57±0.2°, 31.11±0.2°, and 9.99±0.2°.

* * * * *